(12) United States Patent
Stoller et al.

(10) Patent No.: US 11,774,434 B2
(45) Date of Patent: Oct. 3, 2023

(54) SOIL SENSING SYSTEMS AND IMPLEMENTS FOR SENSING DIFFERENT SOIL PARAMETERS

(71) Applicant: Precision Planting LLC, Tremont, IL (US)

(72) Inventors: Jason Stoller, Eureka, IL (US); Ben L. Schlipf, Tremont, IL (US)

(73) Assignee: Precision Planting LLC, Tremont, IL (US)

( * ) Notice: Subject to any disclaimer, the term of this patent is extended or adjusted under 35 U.S.C. 154(b) by 517 days.

(21) Appl. No.: 16/756,434

(22) PCT Filed: Oct. 15, 2018

(86) PCT No.: PCT/US2018/055928
§ 371 (c)(1),
(2) Date: Apr. 15, 2020

(87) PCT Pub. No.: WO2019/079205
PCT Pub. Date: Apr. 25, 2019

(65) Prior Publication Data
US 2021/0190754 A1 Jun. 24, 2021

Related U.S. Application Data

(60) Provisional application No. 62/573,408, filed on Oct. 17, 2017.

(51) Int. Cl.
*A01B 47/00* (2006.01)
*G01N 33/24* (2006.01)
*A01C 7/08* (2006.01)

(52) U.S. Cl.
CPC ............. *G01N 33/24* (2013.01); *A01B 47/00* (2013.01); *A01C 7/08* (2013.01)

(58) Field of Classification Search
CPC ........ G01N 33/24; G01N 33/245; A01C 7/08; A01B 47/00
See application file for complete search history.

(56) References Cited

U.S. PATENT DOCUMENTS 6,484,652 B1 * 11/2002 Colburn, Jr. ......... A01C 21/007
47/1.3
6,608,672 B1    8/2003 Shibusawa et al.
(Continued)

FOREIGN PATENT DOCUMENTS

EP      0254984      *  2/1988  ............... A01C 5/06
EP      2 353 740 A1    8/2011
(Continued)

OTHER PUBLICATIONS

Feng, Sato, Zhang, Liu, Shi, and Zhao, "CMP Antenna Array GPR and Signal-to-Clutter Ratio Improvement", Geoscience and Remote Sensing Letters, IEEE. 6. 23-27. 10.1109/LGRS.2008.2006634.
(Continued)

*Primary Examiner* — Jamie L McGowan

(57) ABSTRACT

Embodiments of the present disclosure relate to systems and implements for sensing, analyzing, and displaying different soil parameters. A soil sensing system includes a mechanical component of an agricultural implement and at least one sensor disposed on the mechanical component. The sensor generates an electromagnetic field through a region of soil as the agricultural implement traverses a field. The sensor comprises at least one radar transmitter and at least one radar receiver and the sensor measures different soil parameters including a soil dielectric constant.

8 Claims, 21 Drawing Sheets

(56) References Cited

U.S. PATENT DOCUMENTS

| | | | |
|---|---|---|---|
| 8,849,523 B1 * | 9/2014 | Chan | A01G 25/167 |
| | | | 701/50 |
| 8,862,339 B2 | 10/2014 | Henry et al. | |
| 2003/0009286 A1 | 1/2003 | Shibusawa et al. | |
| 2003/0184747 A1 | 10/2003 | Diekhans et al. | |
| 2009/0112475 A1 | 4/2009 | Christy et al. | |
| 2015/0094917 A1 | 4/2015 | Blomme et al. | |
| 2015/0247835 A1 * | 9/2015 | Trovat | G01N 33/24 |
| | | | 702/2 |
| 2016/0255763 A1 | 9/2016 | Canyon | |
| 2017/0090068 A1 | 3/2017 | Xiang et al. | |
| 2017/0176589 A1 | 6/2017 | Chan et al. | |
| 2018/0220577 A1 | 8/2018 | Posselius et al. | |
| 2019/0059198 A1 * | 2/2019 | Schnaider | A01B 63/1115 |
| 2019/0208698 A1 * | 7/2019 | Maxton | G01K 7/34 |

FOREIGN PATENT DOCUMENTS

| | | | | |
|---|---|---|---|---|
| EP | 3095310 A1 * | 11/2016 | | A01B 43/00 |
| KR | 2017 0072495 A | 6/2017 | | |
| WO | 2012/102667 A1 | 8/2012 | | |
| WO | 2015/105419 A1 | 7/2015 | | |
| WO | 2015/171908 A1 | 11/2015 | | |
| WO | 2016/077421 A1 | 5/2016 | | |
| WO | 2016/182906 A1 | 11/2016 | | |
| WO | 2017/049186 A1 | 3/2017 | | |
| WO | 2017/158006 A2 | 9/2017 | | |

OTHER PUBLICATIONS

Grote, Hubbard, and Rubin, "Field-scale estimation of volumetric water content using groundpenetrating radar ground wave techniques", Water Resources Research, vol. 39, No. 11, 1321, doi:10.1029/2003WR002045, 2003.

Lambot, Slob, Van Den Bosch, Stockbroeckx and Vanclooster, "Modeling of ground-penetrating Radar for accurate characterization of subsurface electric properties," in IEEE Transactions on Geoscience and Remote Sensing, vol. 42, No. 11, pp. 2555-2568, Nov. 2004, doi: 10.1109/TGRS.2004.834800.

Knight, "Ground Penetrating Radar for Environmental Applications",Annu. Rev. Earth Planet. Sci. 2001. 29:229-55.

Steelman, Endres, and Jones (2012), "High-resolution ground-penetrating radar monitoring of soil moisture dynamics: Field results, interpretation, and comparison with unsaturated flow model", Water Resour. Res., 48, W09538, doi:10.1029/2011WR011414.

USEPA, "Ground-Penetrating Radar", @ https://archive.epa.gov/esd/archive-geophysics/web/html/ground-penetrating_radar.html, last update May 24, 2016.

Geoprospectors, "Topsoil Mapper-Product", @ http://www.geoprospectors.com/gb/products-services/agricultural, viewed on Aug. 2, 2017.

Geoprospectors, "Topsoil Mapper-Applications", @ http://www.geoprospectors.com/gb/products-services/agricultural, viewed on Aug. 2, 2017.

Flatearth Inc., "Chipotle Radar Development Kit" @https://store/flatearthinc.com/collections/chips-salsa/products/chipotle-radar-development-kit, viewed on Aug. 2, 2017.

Flatearth Inc., "Cayenne Radar Development Kit" @https://store/flatearthinc.com/collections/chips-salsa/products/cayenne-radar-development-kit, viewed on Aug. 2, 2017.

Authors "Ground-Penetrating Radar, A Comparison to Seismic Reflection" power point presentation viewed.

Bradford,Harper, and Brown, "Complex Dielectric Permittivity Measurements from Ground-Penetrating Radar Data to Estimate Snow Liquid Water Content in the Pendular Regime", Water Resources Research, vol. 45, W08403, doi:10.1029/2008WR007341, 2009.

Leinss, Silvan, "Depth, anisotropy, and water equivalent of snow estimated by radar interferometry and polarimetry", https://doi.org/10.3929/ethz-a-010603517, 2015 Doctoral Thesis.

Holbrook, Miller, and Provart, "Estimating snowwater equivalent over long mountain transects using snowmobile-mounted ground-penetrating radar", Geophysics, vol. 81, No. 1 (Jan.-Feb. 2016); P. WA183-WA193, 11 Figs. 10.1190/GEO2015-0121.1.

Gustafsson, Sundstrom, and Lundberg, "Estimation of Snow Water Equivalent of Dry Snowpacks Using a Multi-Offset Ground Penetrating Radar System", 69th Eastern Snow Conference, Frost Valley YMCA, Claryville, New York, USA (2012).

Robertson, Marshall, Roberts, and Tidd, "Measuring Snow Water Equivalent in Wet Snow With Ultrawideband GPR", Proceedings, International Snow Science Workshop, Banff, 2014.

Marshall and Robertson, "Continuous Real-Time Snow Properties With Ground Penetrating Radar", Proceedings, International Snow Science Workshop, Breckenridge, Colorado, 2016.

Malik, "A Synergic Approach for Estimating Snow Cover Properties for Using Optical and Active/Passive Microwave Observations", International Institute for Geo-Information Science and Earth Observation, Enschede, Netherlands, Mar. 2009.

St. Clair and Holbrook, "Measuring snow water equivalent from common offset GPR records through migration velocity analysis", https://doi.org/10.5194/tc-2017-90—Manuscript under review for journal The Cryosphere Discussion started: Jun. 13, 2017.

European Patent Office, Search Report for related European Application No. EP 18 86 8111, dated Dec. 1, 2020.

US Recieving Office, International Search Report for Parent International Application No. PCT/US2018/055928, dated Feb. 1, 2019.

* cited by examiner

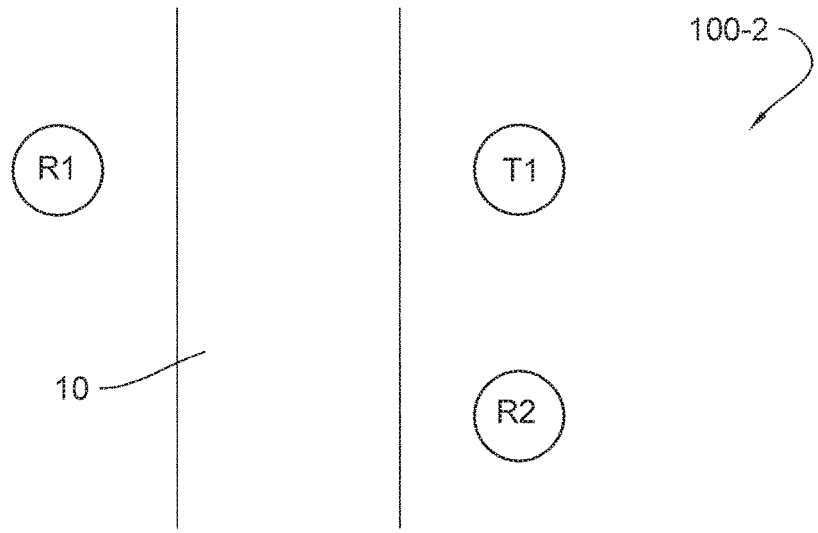
FIG. 3
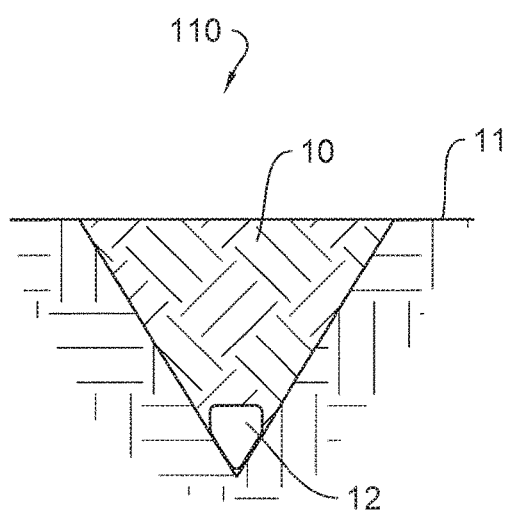 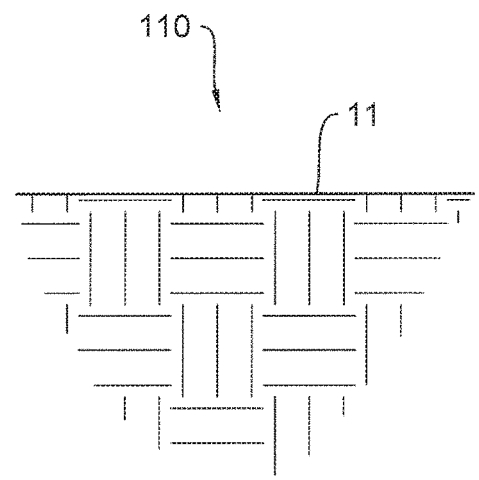
FIG. 4A  FIG. 4B

SOIL SENSING SYSTEMS AND IMPLEMENTS FOR SENSING DIFFERENT SOIL PARAMETERS

RELATED APPLICATIONS

This application claims the benefit of U.S. Provisional Application No. 62/573,408, filed on Oct. 17, 2017 entitled: SOIL SENSING SYSTEMS AND IMPLEMENTS FOR SENSING DIFFERENT SOIL PARAMETERS, the entire contents of which are hereby incorporated by reference.

TECHNICAL FIELD

Embodiments of the present disclosure relate to systems and implements for sensing, analyzing, and displaying different soil parameters.

BACKGROUND

It is well known that proper and uniform seed trench depth, accurate placement of seed within the seed trench (at the proper depth and proper spacing), good seed-to-soil contact, and minimal crop residue within the seed trench are all critical factors in uniform seed emergence and high yields. Accordingly, various planter improvements have been proposed to achieve each of these factors. While conducting spot checks of the seed trench may help to provide some assurances that these critical factors are being achieved, such spot checks will only identify the conditions at the specific location being checked. Accordingly, there is a need for a system that will image the seed trench to verify and ensure these critical factors are being achieved during planting operations and to enable automatic or remote adjustment of the planter while on-the-go based on the images. There is a similar need for below-soil-surfacing-imaging and control for other types of agricultural implements, including tillage implements, sidedress or in-ground fertilizing implements and agricultural data gathering implements.

BRIEF DESCRIPTION OF THE DRAWINGS

The present disclosure is illustrated by way of example, and not by way of limitation, in the Figures of the accompanying drawings and in which:

FIG. 3 schematically illustrates another embodiment of a work layer sensor, in plan view, disposed in relation to a seed trench.

FIGS. 4A-4B are representative examples of work layer images generated by the work layer sensor of FIG. 3.

BRIEF SUMMARY

Embodiments of the present disclosure relate to systems and implements for sensing, analyzing, and displaying different soil parameters.

DETAILED DESCRIPTION

All references cited herein are incorporated herein in their entireties. If there is a conflict between a definition herein and in an incorporated reference, the definition herein shall control. At least one of A, B, and C refers to a selection of A alone, B alone, C alone, a combination of A and B, a combination of A and C, a combination of B and C, or a combination of A and B and C.

Figure 1:
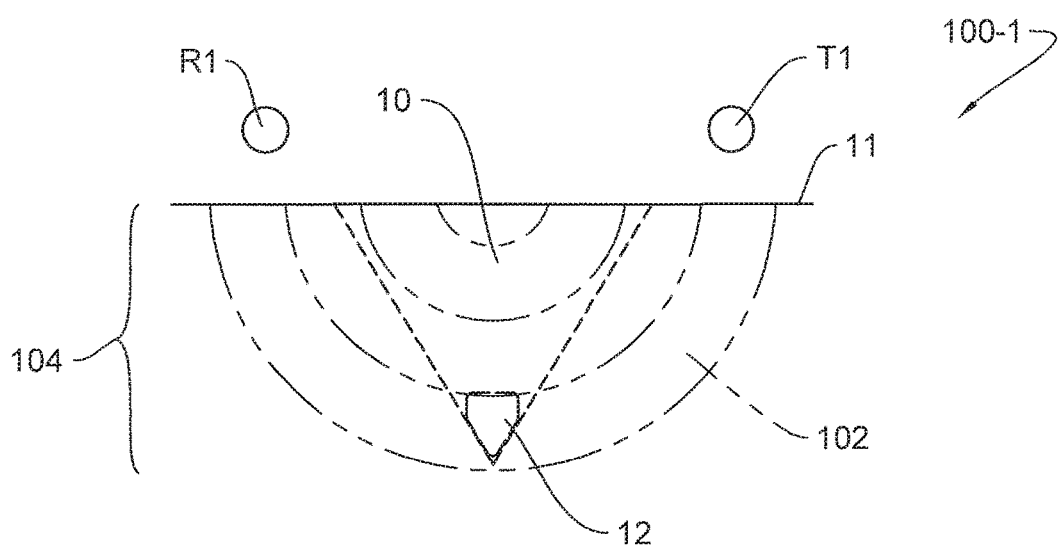
FIG. 1 schematically illustrates one embodiment of a work layer sensor, in elevation view, disposed in relation a seed trench.
Figure 5:
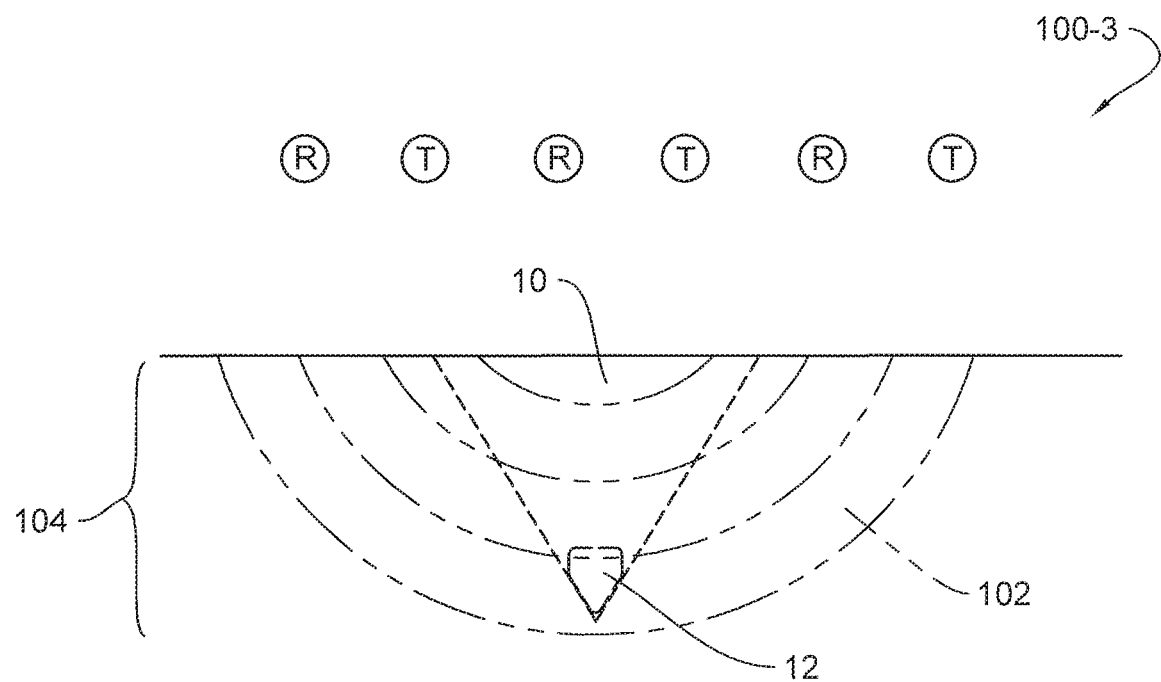
FIG. 5 schematically illustrates another embodiment of a work layer sensor, in elevation view, disposed in relation to a seed trench.

Referring now to the drawings, wherein like reference numerals designate identical or corresponding parts throughout the several views, FIGS. 1, 3 and 5 schematically illustrate alternative embodiments of a work layer sensor 100 to generate a signal or image representative of the soil densities or other soil characteristics throughout a soil region of interest, hereinafter referred to as the "work layer" 104.

The representative image or signal generated by the work layer sensor 100 is hereinafter referred to as the "work layer image" 110. In one particular application discussed later, the work layer sensors 100 may be mounted to a planter row unit 200 (FIG. 7) for generating a work layer image 110 of the seed trench as the planter traverses the field. The work layer image 110 may be displayed on a monitor 300 visible to an operator within the cab of a tractor and the planter may be equipped with various actuators for controlling the planter based on the characteristics of the work layer 104 as determined from the work layer image 110.

The work layer sensor 100 for generating the work layer image 110 may comprise a ground penetrating radar system, an ultrasound system, an audible range sound system, an electrical current system or any other suitable system for generating an electromagnetic field 102 through the work layer 104 to produce the work layer image 110. It should be understood that the depth and width of the work layer 104 may vary depending on the agricultural implement and operation being performed.

FIG. 1 is a schematic illustration of one embodiment of a work layer sensor 100-1 disposed in relation to a seed trench 10 formed in the soil 11 by a planter, wherein the seed trench 10 comprises the soil region of interest or work layer 104. In this embodiment, the work layer sensor 100-1 comprises a transmitter (T1) disposed on one side of the seed trench 10 and a receiver (R1) disposed on the other side of the seed trench 10 to produce the electromagnetic field 102 through the seed trench to generate the work layer image 110.

In some embodiments, the work layer sensor 100 may comprise a ground-penetration radar subsurface inspection system such as any of the following commercially available systems: (1) the StructureScan™ Mini HR available from GSSI in Nashua, N.H.; (2) the 3d-Radar GeoScope™ Mk IV coupled to a 3d-Radar VX-Series and/or DX-Series multi-channel antenna, all available from 3d-Radar AS in Trondheim, Norway; or (3) the MALA Imaging Radar Array System available from MALA Geoscience in Mala, Sweden. In such embodiments, the commercially available system may be mounted to the planter or other implement, or may be mounted to a cart which moves with the implement; in either case the system is preferably disposed to capture an image of a work layer in the area of interest (e.g., the seed trench). In some embodiments, the work layer image 110 may be generated from the signal outputs of the work layer sensor 100 using commercially available software such as GPR-SLICE (e.g., version 7.0) available from GeoHiRes International Ltd. located in Borken, Germany.

Figure 2A:
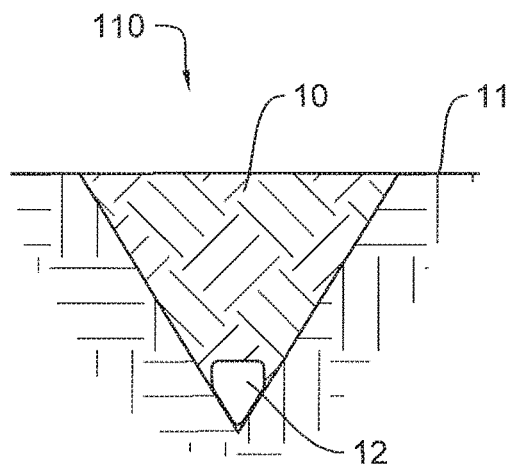
FIGS. 2A-2C are representative examples of work layer images generated by the work layer sensor of FIG. 1.
Figure 2B:
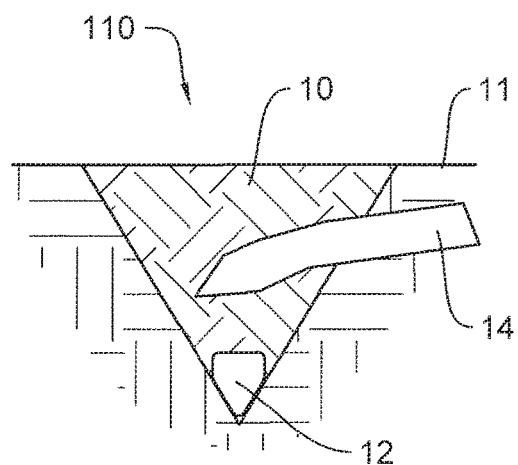
Figure 2C:
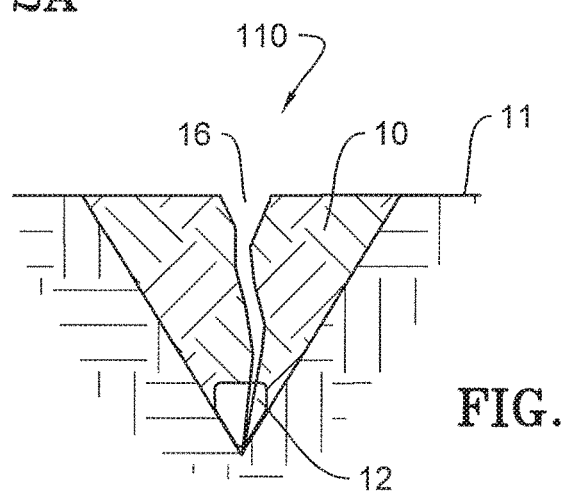

FIGS. 2A-2C are intended to be representative examples of work layer images 110 generated by the work layer sensor 100-1 of FIG. 1 showing various characteristics of the seed trench 10, including, for example, the trench depth, the trench shape, depth of seed 12, the seed depth relative to the trench depth, crop residue 14 in the trench, and the void spaces 16 within the trench. As described in more detail later, the work layer images 110 may be used to determine other characteristics of the work layer 104, including, for example, the seed-to-soil contact, percentage of trench closed, percentage of upper half of trench closed, percentage of lower half of trench closed, moisture of the soil, etc.

FIG. 3 schematically illustrates, in plan view, another embodiment of a work layer sensor 100-2 disposed with respect to a seed trench 10. In this embodiment, a transmitter (T1) is disposed on one side of the seed trench 10, a first receiver (R1) is disposed on the other side of the seed trench 10, and a second receiver (R2) is disposed adjacent and rearward of the transmitter (T1). FIG. 4A is a representative illustration of the work layer image 110 generated through the trench between the transmitter (T1) and the first receiver (R1)) and FIG. 4B is a representative illustration of the work layer image 110 generated between the transmitter (T1) and the second receiver (R2) providing an image of the undisturbed soil adjacent to the seed trench.

FIG. 5 is an elevation view schematically illustrating another work layer sensor embodiment 100-3 disposed with respect to a seed trench 10. In this embodiment, the work layer sensor 100-3 comprises a plurality of transmitter and receiver pairs disposed above and transverse to the seed trench 10.

Figure 6:
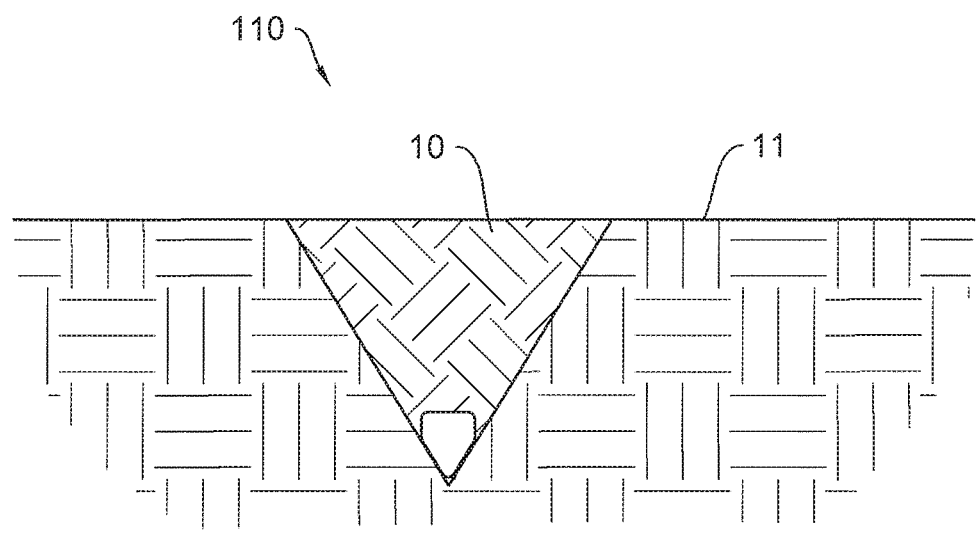
FIG. 6 is a representative example of a work layer image generated by the work sensor of FIG. 5.

FIG. 6 is a representative illustration of the work layer image 110 generated by the work layer sensor 100-3 of FIG. 5 which provides a view not only of the seed trench but also a portion of the soil adjacent to each side of the seed trench.

Figure 10:
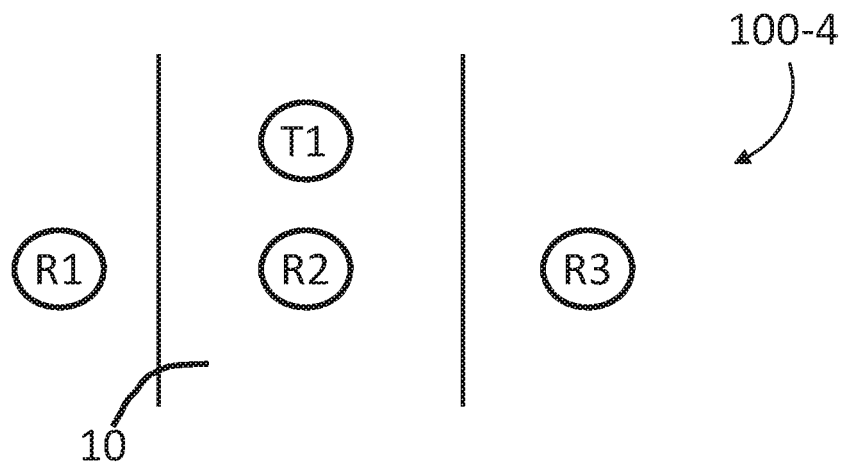
FIG. 10 schematically illustrates another embodiment of a work layer sensor, in plan view, disposed in relation to a seed trench.

FIG. 10 schematically illustrates, in plan view, another embodiment of a work layer sensor 100-4 disposed with respect to a seed trench 10. In this embodiment, a transmitter (T1) is disposed over the seed trench 10. Disposed rearward to transmitter (T1) in a direction of travel are three receivers (R1), (R2), and (R3). Receivers (R1) and (R3) are disposed over each side of seed trench 10, respectively. Receiver (R2) is disposed over seed trench 10. Work layer images similar to those shown in FIGS. 2A to 2C can be generated by work layer sensor 100-4.

Figure 11:
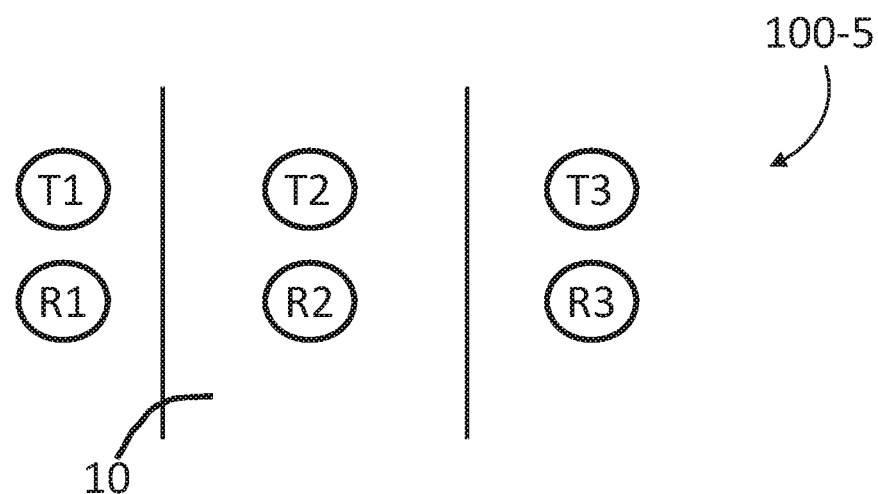
FIG. 11 schematically illustrates another embodiment of a work layer sensor, in plan view, disposed in relation to a seed trench.

FIG. 11 schematically illustrates, in plan view, another embodiment of a work layer sensor 100-5 disposed with respect to a seed trench 10. In this embodiment, transmitter (T2) is disposed over the seed trench 10, and transmitters (T1) and (T3) are disposed over each side of seed trench 10, respectively. Disposed rearward to transmitters (T1), (T2), and (T3) in a direction of travel are three receivers (R1), (R2), and (R3). Receivers (R1) and (R3) are disposed over each side of seed trench 10, respectively. Receiver (R2) is disposed over seed trench 10. Work layer images similar to those shown in FIGS. 2A to 2C can be generated by work layer sensor 100-5.

Figure 12:
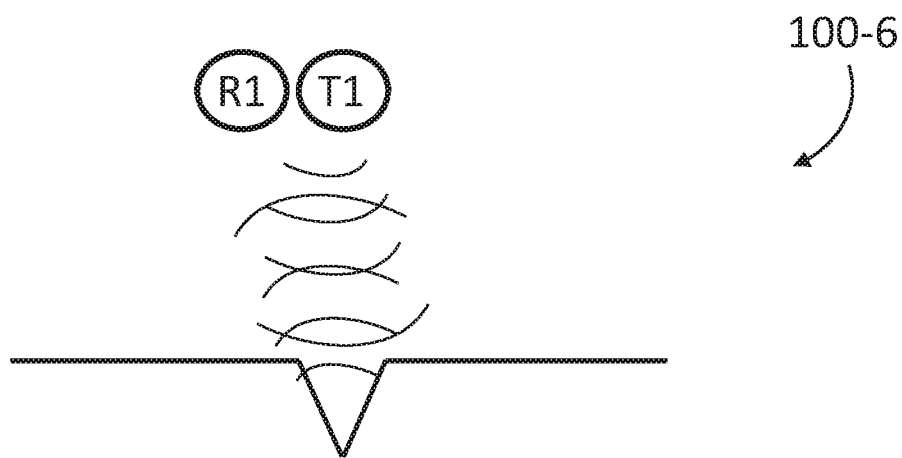
FIG. 12 schematically illustrates another embodiment of a work layer sensor, in side view, disposed in relation to a seed trench.

FIG. 12 schematically illustrates, in side view, another embodiment of a work layer sensor 100-6 disposed with respect to seed trench 10. In this embodiment, transmitter (T1) is disposed over the seed trench 10 and has a transmitting angle that encompasses both sides of seed trench 10. Receiver (R1) can be disposed adjacent to or rearward to transmitter (T1). By having a transmitting angle that reaches both sides of seed trench 10, the reflected signal received by receiver (R1) is then an average of both sides of seed trench 10. This provides a single measurement that is an average of the distance from the transmitter (T1) to the seed trench 10.

Figure 15:
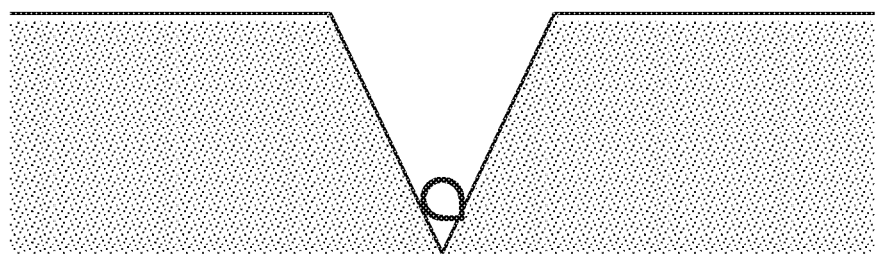
FIG. 15 is representative example of work layer image generated by any of the work layer sensors.

Any of the work layer sensor embodiments 100-1, 100-2, 100-3, 100-4, 100-5, 100-6 can also produce a work layer image as illustrated in FIG. 15. FIG. 15 is a profile of an open seed trench 10, shown with an optional seed.

Figure 13:
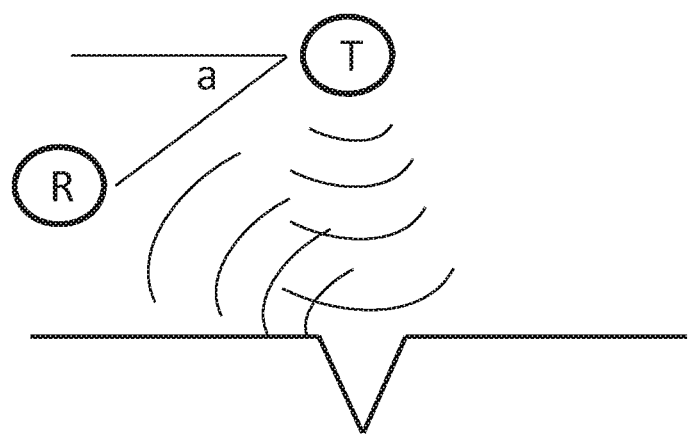
FIG. 13 schematically illustrates, in side view, a spatial relationship between a transmitter and a receiver.

For each of the work layer sensor embodiments 100-1, 100-2, 100-3, 100-4, 100-5, 100-6 the frequency of operation of the work layer sensors 100 and the vertical position of the transmitters (T) and receivers (R) above the soil and the spacing between the transmitters (T) and receivers (R) are selected to minimize signal to noise ratio while also capturing the desired depth and width of the soil region of interest (the work layer 104) for which the work layer image 110 is generated. In an embodiment illustrated in FIG. 13, the height of the receiver (R) above the ground can be less than the height of the transmitter (T) above the ground. An angle a formed between the transmitter (T) and the receiver (R) can be 0 up to 80°.

Figure 14:
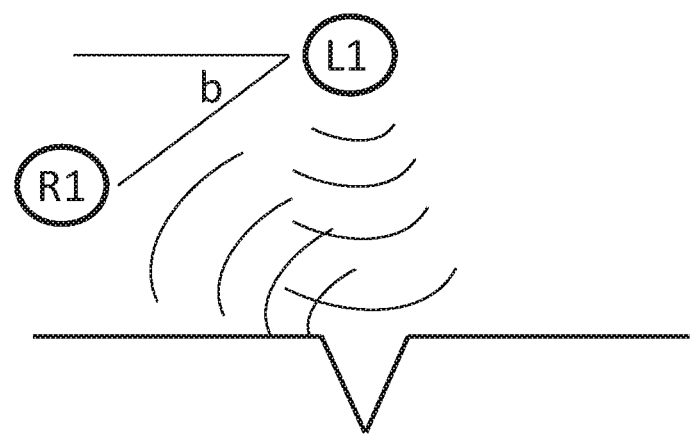
FIG. 14 schematically illustrates another embodiment, in side view, of a laser system.

In an embodiment illustrated in FIG. 14, a laser (L1) is positioned above a seed trench 10 and projects a laser into seed trench 10. A receiver (R1), such as a camera, is positioned to receive the reflected laser signal. Receiver (R1) is at a height above ground that is less than the height of laser (L1) above the ground. An angle b formed between the laser (L1) and the receiver (R) can be greater than 0 up to 80°. The same control system can be used, with laser (L1) replacing a transmitter (T).

In one embodiment, the transmitter frequency selected can be one that can penetrate vegetation and see the soil below. By not seeing the vegetation, a more accurate measurement is obtained for the depth of seed trench 10. It has been determined that the higher the frequency, the more the radar signal is reflected by vegetation. In one embodiment, the frequency is 24 GHz. In another embodiment, the frequency selected can be one that can penetrate dust. Dust can be generated as an agricultural vehicle traverses a field. Frequencies in a range of 1 to 100 GHz can penetrate dust. In any of the work layer sensor embodiments 100-1, 100-2, 100-3, 100-4, 100-5, 100-6, any of the transmitters (T) or receivers (R) can have a frequency that penetrates vegetation and dust. In another embodiment, any of the work layer sensor embodiments 100-1, 100-2, 100-3, 100-4, 100-5 any of the transmitters (T) or receivers (R) can be replaced by multiple transmitters (T) or receivers (R) at the locations illustrated with each transmitter (T) or receiver (R) having a different frequency, such as one that will penetrate through vegetation and one that will penetrate through dust. A composite of the two work layers can be used to generate the profile of seed trench 10.

In one embodiment, the radar is Doppler radar. Doppler radar can provide the speed of a row unit 200, which can then be used in a control system to change the rate of application of an agricultural input to obtain a selected application per linear distance or area. Agricultural inputs include, but are not limited to, seed, fertilizer, insecticide, herbicide, and fungicide. The Doppler radar can be coherent pulsed, pulse-Doppler, continuous wave, or frequency modulation. The Doppler radar can be used with any of work layer sensor embodiments 100-1, 100-2, 100-3, 100-4, 100-5, 100-6.

In one embodiment, the radar is a phased array radar. With a phased array radar, the signals generated by the phased array can be moved from side to side in seed trench 10 to provide a more detailed profile of seed trench 10. The phased array radar can be used with any of work layer sensor embodiments 100-1, 100-2, 100-3, 100-4, 100-5, 100-6.

Figure 7:
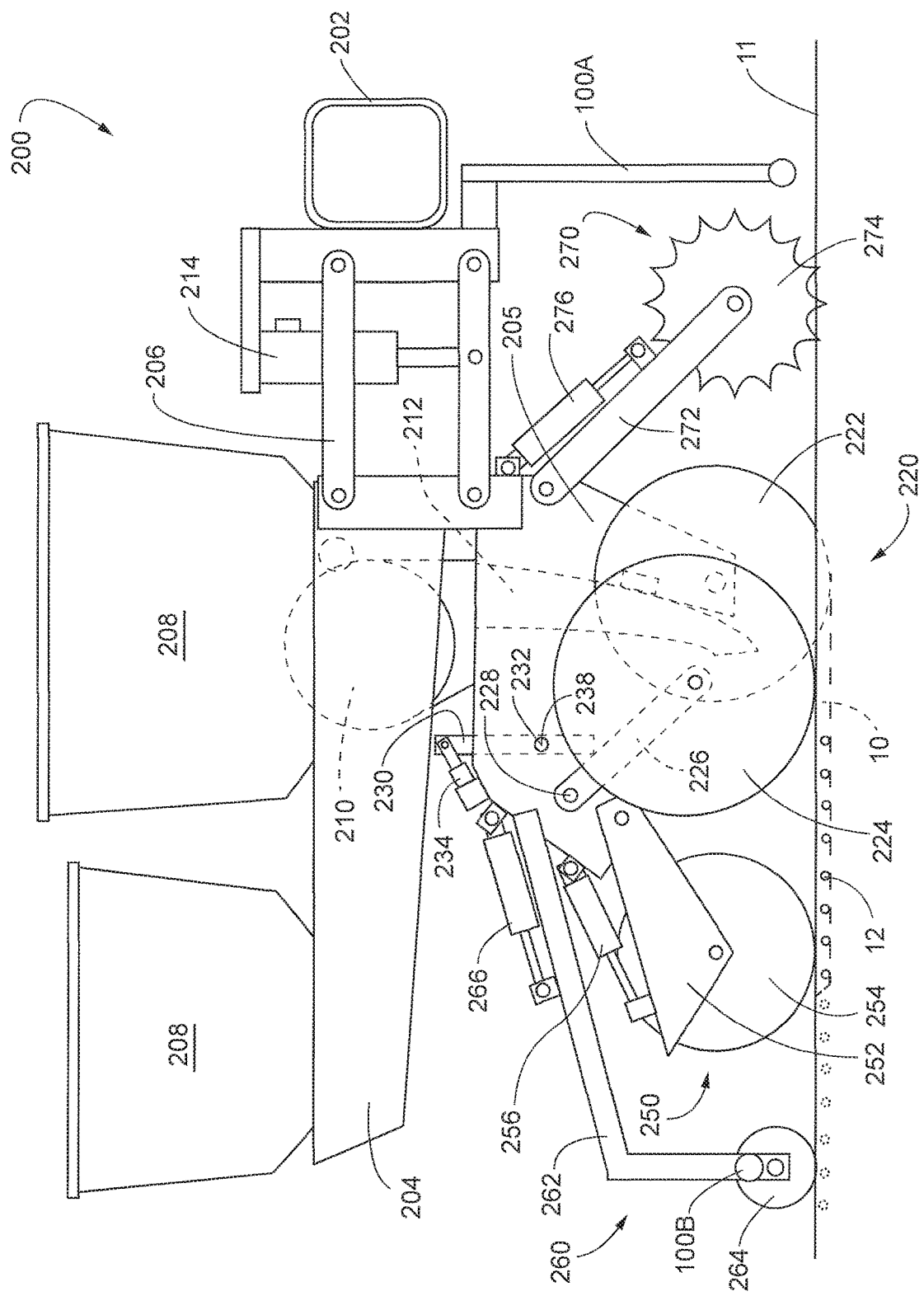
FIG. 7 is a side elevation view of an embodiment of a row unit of an agricultural planter incorporating a work layer sensor of FIG. 1, 3 or 5.

Planter Applications FIG. 7 illustrates one example of a particular application of the work layer sensors 100 disposed on a row unit 200 of an agricultural planter. The row unit 200 includes a work layer sensor 100A disposed on a forward end of the row unit 200 and a work layer sensor 100B disposed rearward end of the row unit 200. The forward and rearward work layer sensors 100A, 100B may comprise any of the embodiments of the work layer sensors 100-1, 100-2, 100-3, 100-4, 100-5, 100-6 previously described.

The forward work layer sensor 100A is disposed to generate a reference work layer image (hereinafter a "reference layer image") 110A of the soil prior to the soil being disturbed by the planter, whereas the rearward work layer sensor 100B generates the work layer image 110B, which in this example, is the image of the closed seed trench 10 in which the seed has been deposited and covered with soil. For the reasons explained later, it is desirable to obtain both a reference image 110A and the work layer image 110B for analysis of the soil characteristics through the work layer 104.

It should be appreciated that the forward and rearward work layer sensors 100A, 100B referenced in FIG. 7 may employ any of the embodiments 100-1, 100-2 or 100-3.100-4, 100-5, 100-6 previously described. However, it should be appreciated that if the embodiments 100-2, 100-3, 100-4, or 100-5 are employed, the forward work layer sensor 100A may be eliminated because the embodiments 100-2, 100-3, 100-4, and 100-5 are configured to generate the work layer images 110 of undisturbed soil adjacent to the seed trench 10 which could serve as the reference layer image 110A.

With respect to FIG. 7, the row unit 200 is comprised of a frame 204 pivotally connected to the toolbar 202 by a parallel linkage 206 enabling each row unit 200 to move vertically independently of the toolbar 202. The frame 204 operably supports one or more hoppers 208, a seed meter 210, a seed delivery mechanism 212, a downforce control system 214, a seed trench opening assembly 220, a trench closing assembly 250, a packer wheel assembly 260, and a row cleaner assembly 270. It should be understood that the row unit 200 shown in FIG. 7 may be for a conventional planter or the row unit 200 may be a central fill planter, in which case the hoppers 208 may be replaced with one or more mini-hoppers and the frame 204 modified accordingly as would be recognized by those of skill in the art.

The downforce control system 214 is disposed to apply lift and/or downforce on the row unit 200 such as disclosed in U.S. Publication No. US2014/0090585.

The seed trench opening assembly 220 includes a pair of opening discs 222 rotatably supported by a downwardly extending shank member 205 of the frame 204. The opening discs 222 are arranged to diverge outwardly and rearwardly so as to open a v-shaped trench 10 in the soil 11 as the planter traverses the field. The seed delivery mechanism 212, such as a seed tube or seed conveyor, is positioned between the opening discs 222 to deliver seed from the seed meter 210 and deposit it into the opened seed trench 10. The depth of the seed trench 10 is controlled by a pair of gauge wheels 224 positioned adjacent to the opening discs 222. The gauge wheels 224 are rotatably supported by gauge wheel arms 226 which are pivotally secured at one end to the frame 204 about pivot pin 228. A rocker arm 230 is pivotally supported on the frame 204 by a pivot pin 232. It should be appreciated that rotation of the rocker arm 230 about the pivot pin 232 sets the depth of the trench 10 by limiting the upward travel of the gauge wheel arms 226 (and thus the gauge wheels) relative to the opening discs 222. The rocker arm 230 may be adjustably positioned via a linear actuator 234 mounted to the row unit frame 204 and pivotally coupled to an upper end of the rocker arm 230. The linear actuator 234 may be controlled remotely or automatically actuated as disclosed, for example, in International Publication No. WO2014/186810.

A downforce sensor 238 is configured to generate a signal related to the amount of force imposed by the gauge wheels 224 on the soil. In some embodiments the pivot pin 232 for the rocker arm 230 may comprise the downforce sensor 238, such as the instrumented pins disclosed in U.S. Pat. No. 8,561,472. The seed meter 210 may be any commercially available seed meter, such as the fingertype meter or vacuum seed meter, such as the vSet® meter, available from Precision Planting LLC, 23207 Townline Rd, Tremont, Ill. 61568.

The trench closing assembly 250 includes a closing wheel arm 252 which pivotally attaches to the row unit frame 204. A pair of offset closing wheels 254 are rotatably attached to the closing wheel arm 252 and angularly disposed to direct soil back into the open seed trench so as to "close" the soil trench. An actuator 256 may be pivotally attached at one end to the closing wheel arm 252 and at its other end to the row unit frame 204 to vary the down pressure exerted by the closing wheels 254 depending on soil conditions. The closing wheel assembly 250 may be of the type disclosed in International Publication No. WO2014/066650.

The packer wheel assembly 260 comprises an arm 262 pivotally attached to the row unit fame 204 and extends rearward of the closing wheel assembly 250 and in alignment therewith.

The arm 262 rotatably supports a packer wheel 264. An actuator 266 is pivotally attached at one end to the arm and at its other end to the row unit frame 204 to vary the amount of downforce exerted by the packer wheel 264 to pack the soil over the seed trench 10.

The row cleaner assembly 270 may be the CleanSweep® system available from Precision Planting LLC, 23207 Townline Rd, Tremont, Ill. 61568. The row cleaner assembly 270 includes an arm 272 pivotally attached to the forward end of the row unit frame 204 and aligned with the trench opening assembly 220. A pair of row cleaner wheels 274 are rotatably attached to the forward end of the arm 272. An actuator 276 is pivotally attached at one end to the arm 272 and at its other end to the row unit frame 204 to adjust the downforce on the arm to vary the aggressiveness of the action of the row cleaning wheels 274 depending on the amount of crop residue and soil conditions.

It should be appreciated that rather than positioning the work layer sensors 100 as shown in FIG. 7, the work layer sensors may be positioned after the row cleaner assembly 270 and before the trench opening assembly 220 or in one or more other locations between the trench opening discs 222 and the closing wheels 254 or the packing wheel 264 depending on the soil region or characteristics of interest.

Figure 8:
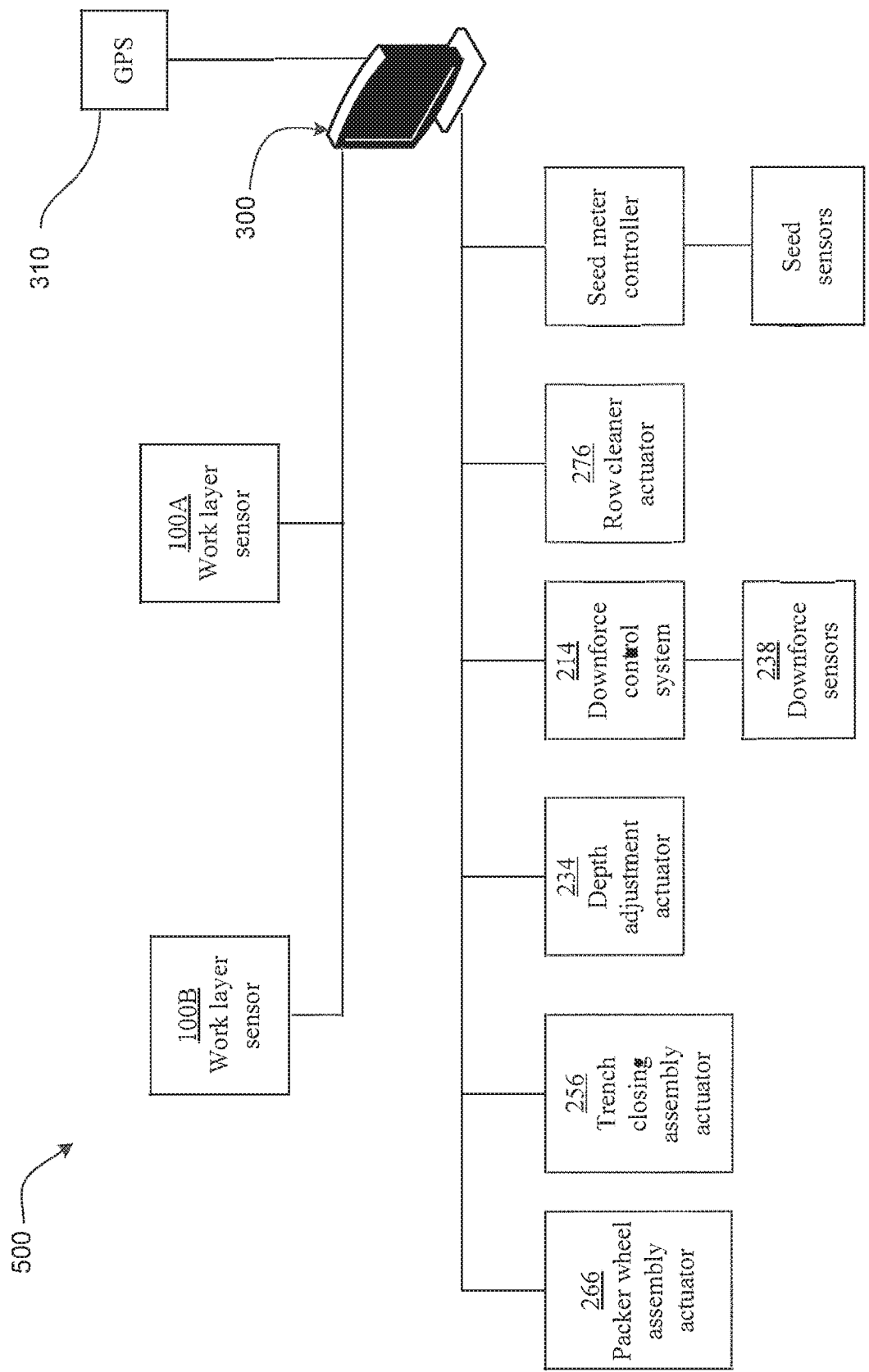
FIG. 8 illustrates an embodiment of a work layer implement monitoring, control and operator feedback system.

Planter Control and Operator Feedback FIG. 8 is a schematic illustration of a system 500 which employs work layer sensors 100 to provide operator feedback and to control the planter row unit 200. Work layer sensors 100A, 100B are disposed to generate a reference layer image 110A of undisturbed soil and a work layer image 110B of the closed seed trench (i.e., after seed is deposited, covered with soil by the closing wheel assembly 250 and the soil packed with the packing wheel assembly 260). As previously described, the work layer sensors 100A, 100B may be separate work layer sensors disposed forward and rearward of the row unit 200 as illustrated in FIG. 7, or the work layer sensors 100A, 100B may comprise a single work layer sensor with transmitters (T) and receivers (R) disposed to generate both a reference layer image 110A and a work layer image 110B.

The work layer image 110B may be communicated and displayed to the operator on a monitor 300 comprising a display, a controller and user interface such as a graphical user interface (GUI), within the cab of the tractor.

The monitor 300 may be in signal communication with a GPS unit 310, the row cleaner actuator 276, the downforce control system 214, the depth adjustment actuator 234, the trench closing assembly actuator 256 and the packer wheel assembly actuator 266 to enable operational control of the planter based on the characteristics of the work layer image 110B. For example, if the work layer image 110B indicates that residue in the seed trench 10 is above a predetermined threshold (as explained below), a signal is generated by the monitor 300 to actuate the row cleaner actuator 276 to increase row cleaner downforce. As another example, if the seed depth is less than a predetermined threshold (as explained below), a signal is generated by the monitor 300 to actuate the downforce control system 214 to increase the downforce and/or to actuate the depth adjustment actuator 234 to adjust the gauge wheels 224 relative to the opening discs 222 to increase the trench depth. Likewise if the seed depth is greater than a predetermined threshold, a signal is generated by the monitor 300 to actuate the downforce control system 214 to decrease the downforce and/or to actuate the depth adjustment actuator 234 to decrease the trench depth. As another example, if the upper portion of the trench has more than a threshold level of void space (as explained below), a signal is generated by the monitor 300 to actuate the trench closing wheel assembly actuator 256 to increase the downforce on the closing wheels 254. As another example, if the lower portion of the trench has more than a threshold level of void space (as explained below), a signal is generated by the monitor 300 to actuate the packer wheel assembly actuator 266 to increase the downforce on the packer wheel 264.

In still other examples, the work layer image 110B may identify and/or analyze (e.g., determine depth, area, volume, density or other qualities or quantities of) subterranean features of interest such as tile lines, large rocks, or compaction layers resulting from tillage and other field traffic. Such subterranean features may be displayed to the user on the monitor 300 and/or identified by the monitor 300 using an empirical correlation between image properties and a set of subterranean features expected to be encountered in the field. In one such example, the area traversed by the gauge wheels (or other wheels) of the planter (or tractor or other implement or vehicle) may be analyzed to determine a depth and/or soil density of a compaction layer beneath the wheels. In some such examples, the area of the work layer image may be divided into subregions for analysis based on anticipated subterranean features in such sub-regions (e.g., the area traversed by the gauge wheels may be analyzed for compaction).

In other examples, the monitor 300 may estimate a soil property (e.g., soil moisture, organic matter, or electrical conductivity, water table level) based on image properties of the work layer image 110B and display the soil property to the user as a numerical (e.g., average or current) value or a spatial map of the soil property at geo-referenced locations in the field associated with each soil property measurement (e.g., by correlating measurements with concurrent geo-referenced locations reported the GPS unit 310).

Alternatively or additionally, the monitor 300 could be programmed to display operational recommendations based on the characteristics of the work layer image 110B. For example, if the work layer image 110B identifies that the seed 12 is irregularly spaced in the trench 10 or if the seed 12 is not being uniformly deposited in the base of the trench, or if the spacing of the seed 12 in the trench does not match the anticipated spacing of the seed based on the signals generated by the seed sensor or speed of the seed meter, such irregular spacing, nonuniform positioning or other inconsistencies with anticipated spacing may be due to excess speed causing seed bounce within the trench or excess vertical acceleration of the row unit. As such, the monitor 300 may be programmed to recommend decreasing the planting speed or to suggest increasing downforce (if not automatically controlled as previously described) to reduce vertical acceleration of the planter row units. Likewise to the extent the other actuators 276, 214, 234, 256, 266 are not integrated with the monitor controller, the monitor may be programmed to display recommendations to the operator to make manual or remote adjustments as previously described based on the characteristics of the work layer image 110B.

Figure 9:
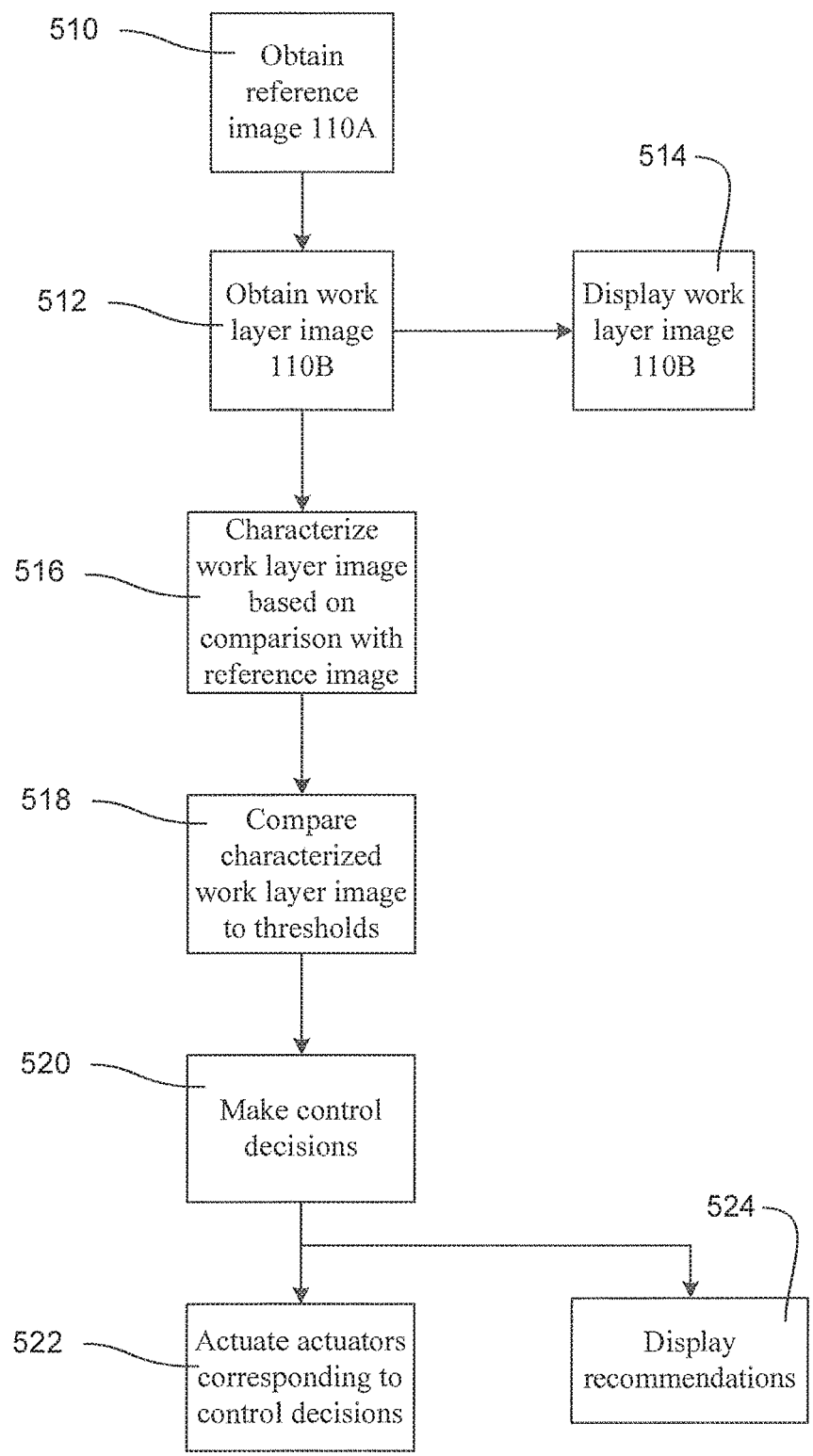
FIG. 9 is a chart showing a process for work layer implement monitoring, control and operator feedback.

FIG. 9 illustrates the process steps for controlling the planter and providing operator feedback. At steps 510 and 512, the reference image 110A and work layer image 110B is generated by the work image sensor(s) 100. At step 514, the work layer image 110B may be displayed to the operator on the monitor 300 in the cab of the tractor. At step 516, the reference layer image 110A is compared with the work layer image 110B to characterize the work layer image. At step 518, the characterized work layer image 110B is compared to predetermined thresholds. At step 520, control decisions are made based on the comparison of the characterized work layer image 110B with the predetermined thresholds. At step 522, the planter components may be controlled by the monitor 300 generating signals to actuate one or more of the corresponding actuators 276, 214, 234, 256, 266 and/or at step 524, corresponding recommendations may be displayed to the operator on the monitor display.

To characterize the work layer image 110B at step 516, the monitor 300 compares one or more characteristics (e.g., density) of the reference image 110A with the same characteristics of the work layer image 110B. In some embodiments, a characterized image may be generated comprising only portions of the work layer image differing from the reference image by at least a threshold value. The characterized image may then be used to identify and define features of the work layer image 110B, such as the trench shape, the trench depth, residue in the trench, seeds and seed placement within the trench, void spaces within the trench, and density differences of the soil within the trench.

For example, to determine the seed depth, the seed is identified or identifiable from the work layer image 110B by determining regions within the work layer image having a size or shape corresponding to a seed and having a density range empirically corresponding to seed. Once a region is identified as a seed, the vertical position of the seed with respect to the soil surface is readily measurable or determined.

As another example, the amount of residue in the trench can be determined by (a) defining the area of the trench cross-section (based on soil density differences between the reference image 110A and the work layer image 110B); (b) by identifying the regions within the trench having a density range empirically corresponding to residue; (c) totaling the area of the regions corresponding to residue; and (d) dividing the residue area by the trench cross-sectional area.

Other Applications—It should be appreciated that work layer sensors 100 may be employed with other agricultural implements and operations, such as, for example, tillage operations and/or side-dress fertilization operations, or in connection with agricultural data gathering operations to view or analyze below-surface soil characteristics, seed placement, root structure, location of underground water-management features such as tiling, etc.

When employed with tillage implements, the work layer sensors 100 may be disposed forward of any tillage tools (i.e., shank, disk, blade, knife, spoon, coulter, etc.) or between forward and rearward spaced tillage tools and/or rearward of any tillage tools. When employed with sidedress or other in-ground fertilization tools, the work layer sensors 100 may be disposed forward or rearward of any sidedress or in-ground tools (i.e., shank, disk, blade, knife, spoon, coulter, leveling basket harrows, etc.).

When employed with a dedicated measurement implement, the work layer sensors 100 may be disposed above undisturbed soil which may or may not have residue cleared by a row cleaner.

For the tillage implements and sidedress or in-ground fertilization tools, actuators on these implements can be automatically controlled to adjust depth of the tillage tools or the monitor 300 can be programmed to provide feedback or recommendations to the operator to manually adjust or remotely adjust the actuators as described above with respect to the planter application. For example, if the feedback or recommendations to the operator indicate that the depth of the tillage tools should be adjusted, an actuator associated with ground engaging wheels supporting the toolbar or a section of the toolbar may be actuated to raise or lower the toolbar to decrease or increase the depth of penetration of the toolbars. Alternatively, separate actuators may be associated with individual tillage tools to adjust the depth of the individual tillage tools. As another example, if the work layer images indicate that the implement is approaching more dense or compact soil, actuators associated to adjust downforce or pressure may be actuated to increase the downforce as the implement passes through the more dense or compact soil. In other embodiments if the work layer images across the width of the implement indicate that one side or the other is tilling the soil more aggressively, an actuator associated with a wing of the implement may be actuated to ensure balancing of the aggressiveness of tillage tools across the side-to-side width of the implement. Likewise an actuator associated with fore and aft leveling of the implement may be actuated to ensure aggressiveness of tools on the front of the implement are balanced with those on the back. In still other embodiments, actuators may be provided to adjust the angle of attack of a disc gang or wing of a tillage implement, or individual tillage tools depending on the work layer images and operator feedback as the implement traverses the field encountering different soil conditions.

In one embodiment, soil sensing information can be obtained and displayed during agricultural operations. A numeric display (e.g., average or current value) and spatial mapping of depth of soil density change can be provided on an implement (e.g., on a planter, a tillage tool, combine, sprayer, on a tractor pulling a grain wagon, or a tractor pulling any implement). The implement includes a sensor (e.g., radar, electrical conductivity (EC), electromagnetic (EM), force probe, etc.) to measure or calculate at least one of the presence of one or more soil densities existing between 0 and 30" of soil depth, a magnitude of the density layer differences or the soil densities themselves, a rate of change of the soil density layer changes (e.g., abrupt within 1", gradual over 6", etc.), and a soil depth at which each density layer starts or transitions to a different density layer.

In one example, the implement can provide a numeric display (e.g., average or current value) of the above information that is measured by a sensor and calculated by a sensor or another device. The implement can also provide a spatial mapping of the above information at geo-referenced locations in the field associated with each soil property measurement (e.g., by correlating measurements with concurrent geo-referenced locations reported from the GPS unit 310).

Figure 16A:
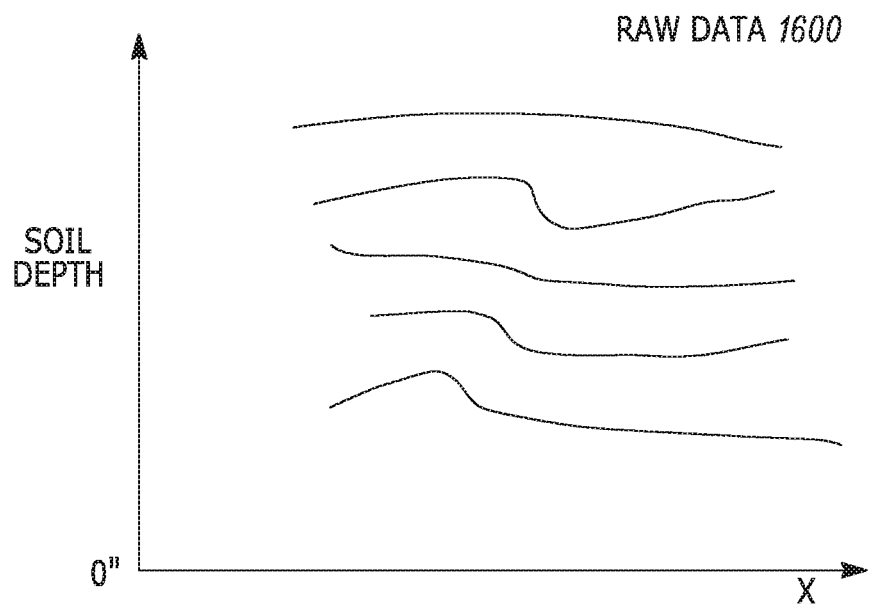
FIG. 16A illustrates raw soil data at different depths in accordance with one embodiment.
Figure 16B:
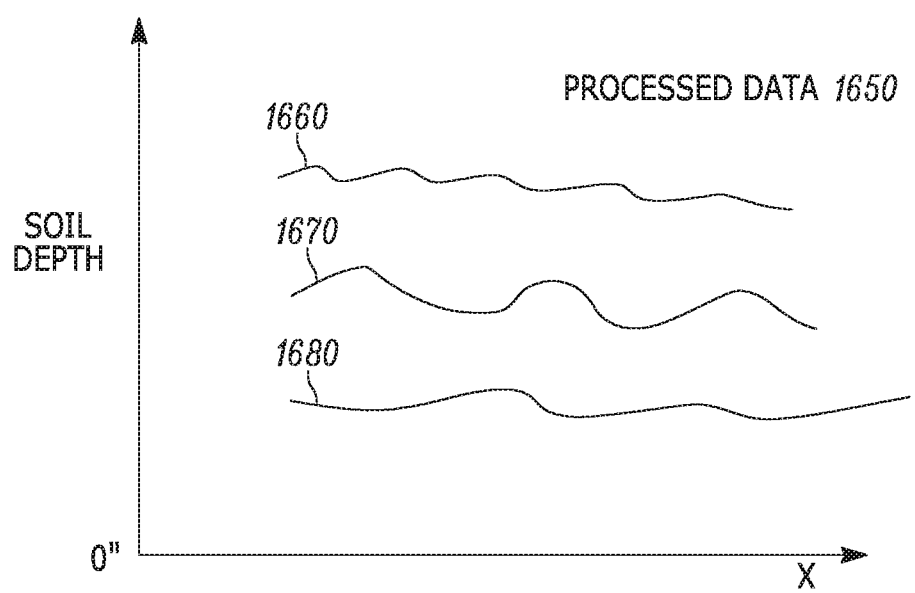
FIG. 16B illustrates processed soil data at different depths in accordance with one embodiment.

In another example, a soil density change at a certain depth can be combined with a sensed moisture level at this depth or combined with soil type or texture to process raw data to generate processed data. FIG. 16A illustrates raw data 1600 and FIG. 16B illustrates processed data 1650 for different depths (e.g., 0 to 30") of soil layers in accordance with one embodiment. The processed data 1650 includes different soil layers 1660, 1670, and 1680 at different soil depths (e.g., 0 to 30 inches). A root or stone may cause a change in soil density within a layer or between layers. Depth of roots during harvest for in row versus out of row can be determined based on soil density.

In another embodiment, a numeric display (e.g., average or current value) and spatial mapping of depth of soil density change can be provided on an implement (e.g., on a planter, a tillage tool, combine, sprayer, on a tractor pulling a grain wagon, or a tractor pulling any implement). The implement includes a sensor (e.g., radar, electrical conductivity (EC), electromagnetic (EM), force probe, etc.) to measure or calculate one or more soil density variabilities (e.g., 0" to 4", 4" to 12", 0" to 10", 0 to 20", etc.).

In one example, the implement can provide a numeric display of the above information that is measured by a sensor and calculated by a sensor or another device. The implement can also provide a spatial mapping of the above information at geo-referenced locations in the field associated with each soil property measurement (e.g., by correlating measurements with concurrent geo-referenced locations reported the GPS unit 310).

In another embodiment, a numeric display (e.g., average or current value) and spatial mapping of depth of soil density change can be provided on an implement (e.g., on a planter, a tillage tool, combine, sprayer, on a tractor, or a tractor pulling any implement). The implement includes a sensor e.g., (radar, electrical conductivity (EC), electromagnetic (EM), force probe, etc.) to measure or calculate at least one of soil density variability, soil surface roughness (measured as Coefficient of Variation), and a residual material thickness (e.g., crop residue). An instantaneous surface roughness may identify an inconsistent surface at a ground level (e.g., 0" depth). The soil surface roughness parameter can be analyzed to determine if a clod of soil at a certain depth (e.g., 0 to 3 inches) causes a change in this parameter. The soil surface roughness parameter (e.g., percentage, visual mapping) can be displayed during tillage or leveling of a field.

The residual material thickness can be compared in row versus out of row for rows of a field. Based on the residual material thickness parameter, a row cleaner down force of a planter may need to be adjusted. A residual material thickness can be displayed to a user while planting seed.

In one example, the implement can provide a numeric display of the above information that is measured by a sensor and calculated by a sensor or another device. The implement can also provide a spatial mapping of the above information at geo-referenced locations in the field associated with each soil property measurement (e.g., by correlating measurements with concurrent geo-referenced locations reported the GPS unit 310).

In one embodiment, a soil GPR (System) uses radar for sensing soil properties by measuring a soil dielectric constant of soil using an implement (e.g., planter, tillage tool, combine, tractor pulling a grain wagon, tractor pulling any implement, etc.). The system includes one or more radar transmitters, receivers, antennas or any combination of transmitters, receivers, and antennas that sense at multiple soil depths (e.g., first soil depth, second soil depth, third soil depth, etc.). Generally, a GPR system operates with a first transmitter radiating a pulse into soil, then the first receiver collects the reflected signal, and this process repeats from every pair of transmitters and receivers. An EC sensor can sense electrical conductivity of soil and this parameter corresponds to soil dielectric constant that is used to convert a transmit/receive time of a radar signal into a distance to determine a soil depth. Radar provides reflections at multiple depths to determine different soil density layers.

GPR is a geophysical method that uses radar pulses to image the subsurface. This nondestructive method uses electromagnetic radiation in the microwave band (UHF/VHF frequencies) of the radio spectrum, and detects the reflected signals from subsurface structures. GPR uses high-frequency (usually polarized) radio waves, usually in the range 10 MHz to 2.6 GHz. A GPR transmitter emits electromagnetic energy into the ground. When the energy encounters a buried object or a boundary between materials having different permittivities, it may be reflected or refracted or scattered back to the surface. A receiving antenna can then record the variations in the return signal. The principles involved are similar to seismology, except GPR methods implement electromagnetic energy rather than acoustic energy, and energy may be reflected at boundaries where subsurface electrical properties change rather than subsurface mechanical properties as is the case with seismic energy. The electrical conductivity of the ground, the transmitted center frequency, and the radiated power all may limit the effective depth range of GPR investigation. Increases in electrical conductivity attenuate the introduced electromagnetic wave, and thus the penetration depth decreases. Higher frequencies do not penetrate as far as lower frequencies due to frequency-dependent attenuation mechanisms though higher frequencies may provide improved resolution.

In another embodiment, soil system includes radar and optical soil sensing. Examples of optical soil sensing can be found in WO2014/153157, WO2015/171908, and U.S. Application Nos. 62/436,342, filed 19 Dec. 2016, 62/446, 254, filed 13 Jan. 2017, and 62/482,116, filed 5 Apr. 2017. The soil system includes one or more radar transmitters, receivers, antennas or any combination of transmitters, receivers, and antennas that sense at multiple soil depths (e.g., first soil depth, second soil depth, third soil depth, etc.). The system further includes multiple radar antennas combined with one or more radar transmitters and receivers or combination transmitters or receivers. The system further includes one or more optical sensors (e.g., breaking of a light beam) to sense soil organic matter, soil moisture, soil texture, and soil cation-exchange capacity (CEC).

In one example, a common midpoint (CMP) antenna array can be utilized by positioning a target at a known depth, generating and receiving EM pulses, and then calculating for that depth.

Figure 17:
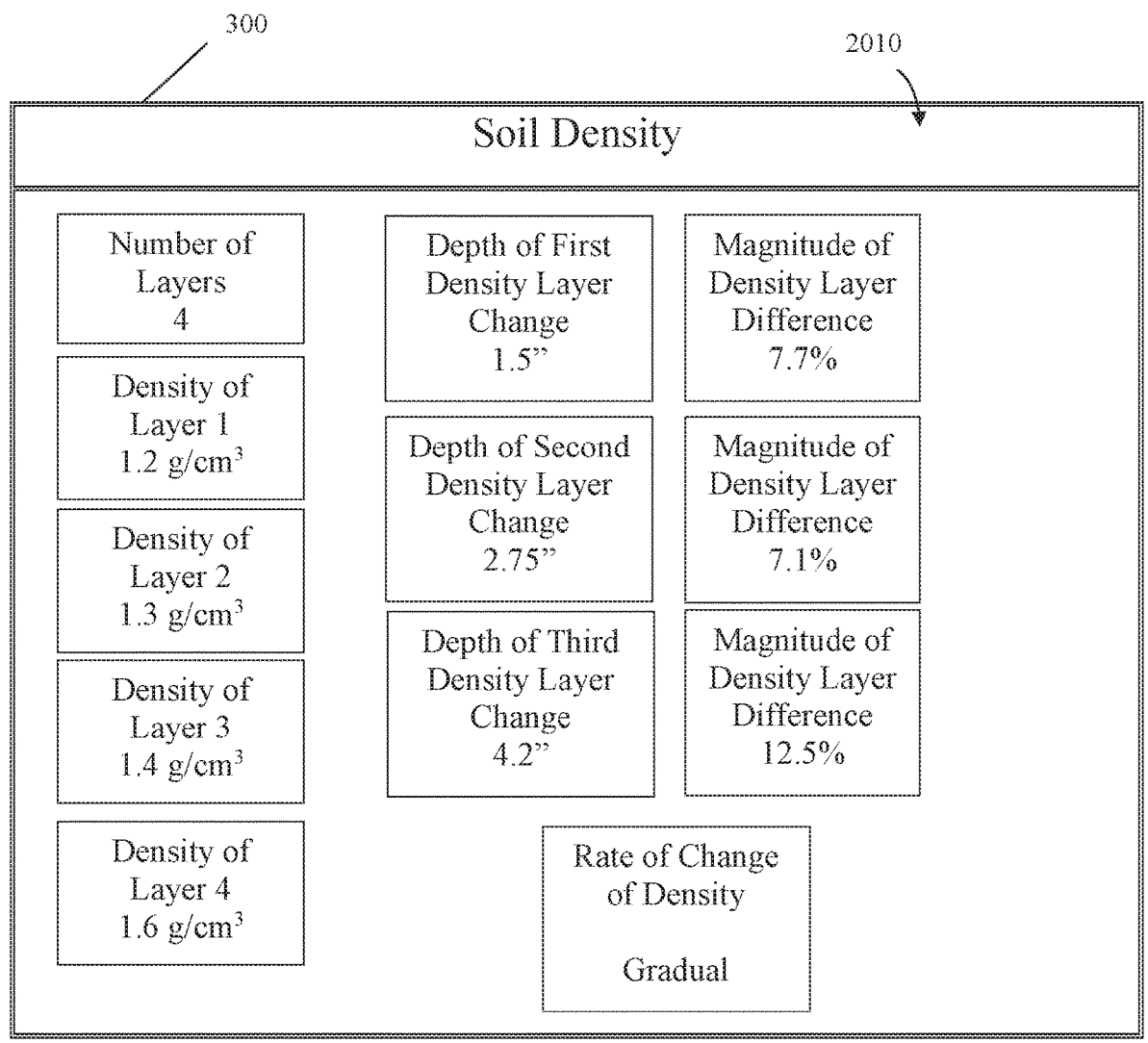
FIG. 17 illustrates a monitor displaying soil density data.
Figure 18:
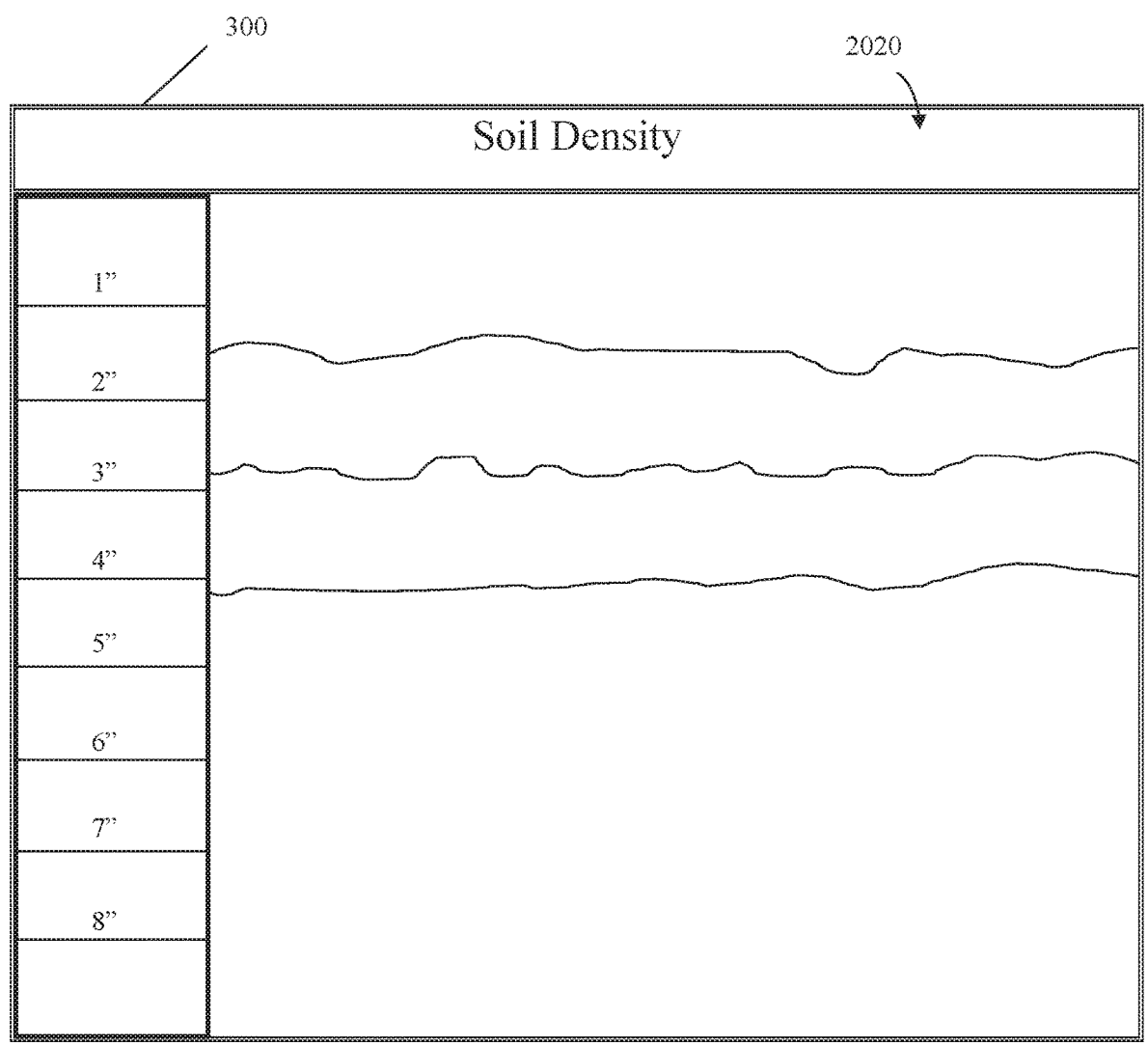
FIG. 18 illustrates a monitor displaying soil density data.
Figure 19:
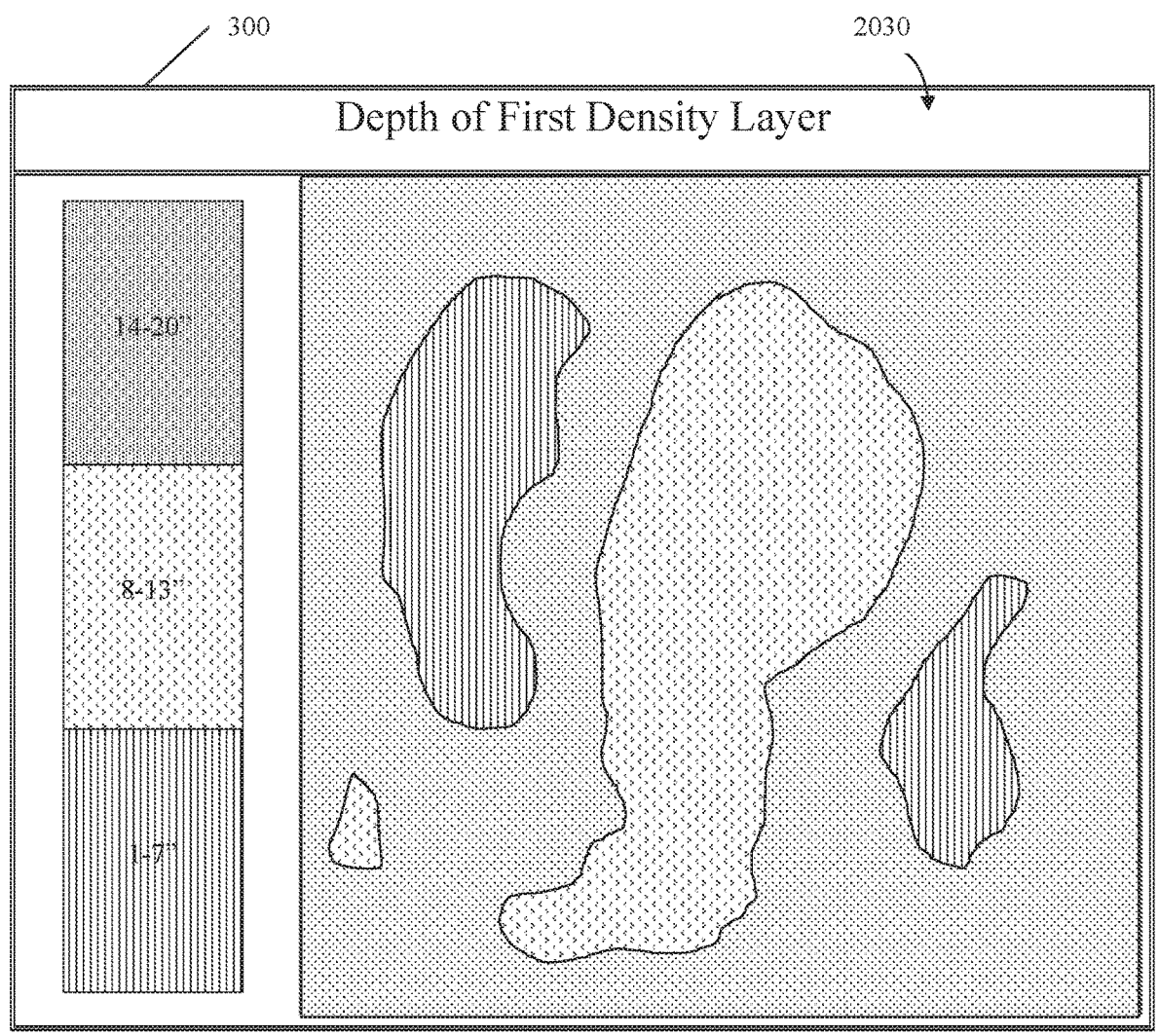
FIG. 19 illustrates a monitor spatially displaying the depth of a first soil density change across a field.
Figure 20:
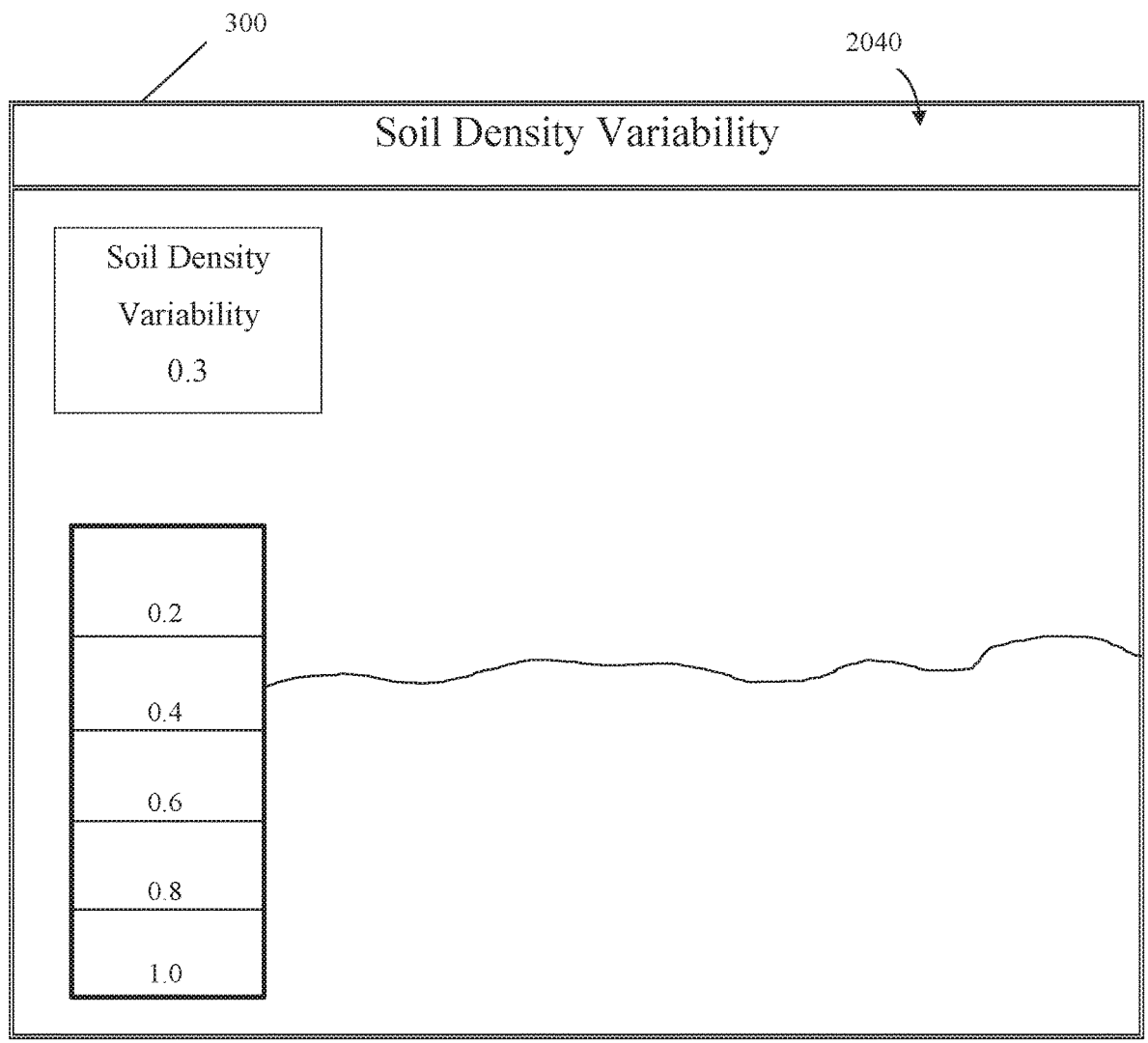
FIG. 20 illustrates a monitor displaying soil density variability.
Figure 21:
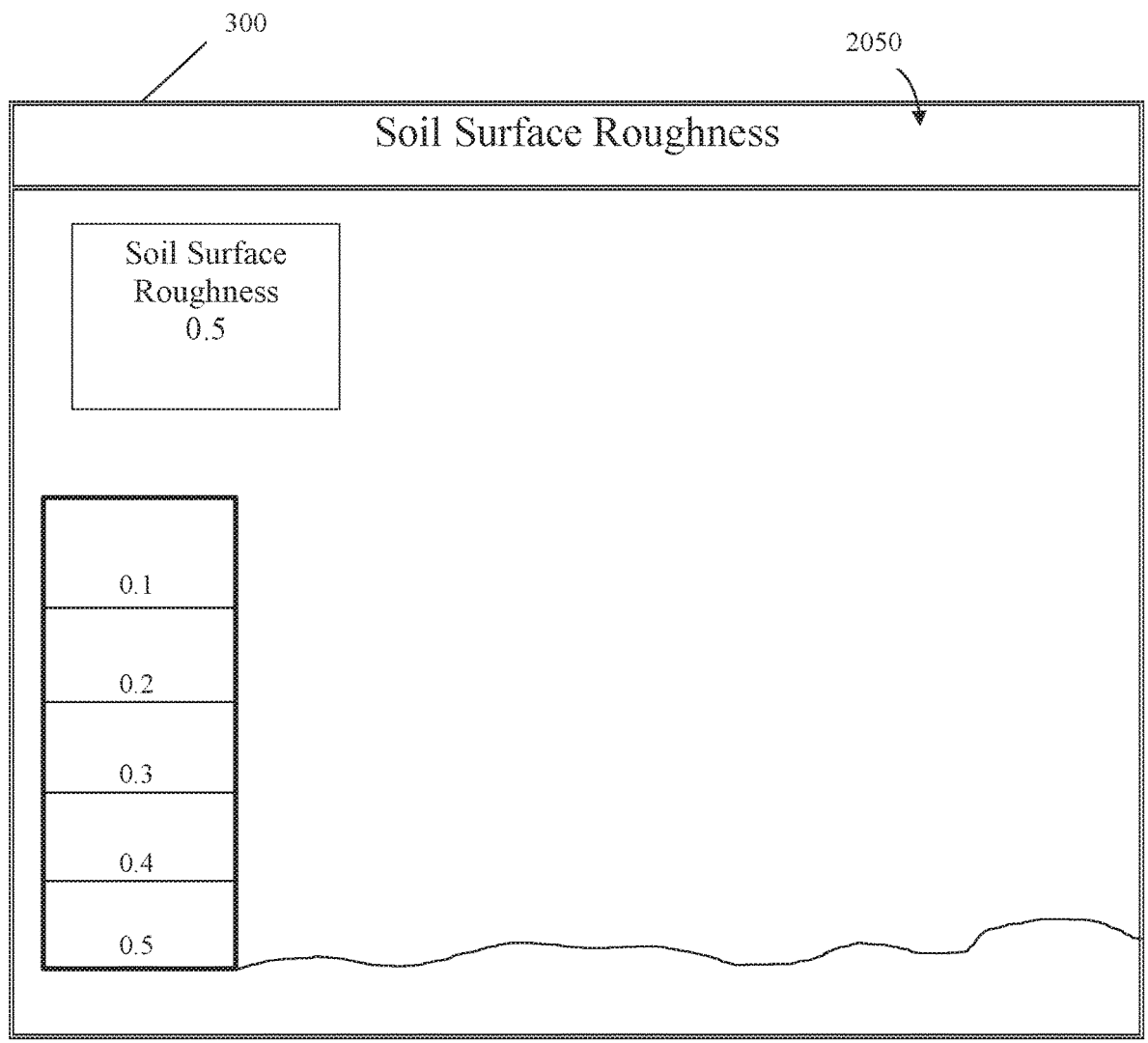
FIG. 21 illustrates a monitor displaying soil surface roughness.
Figure 22:
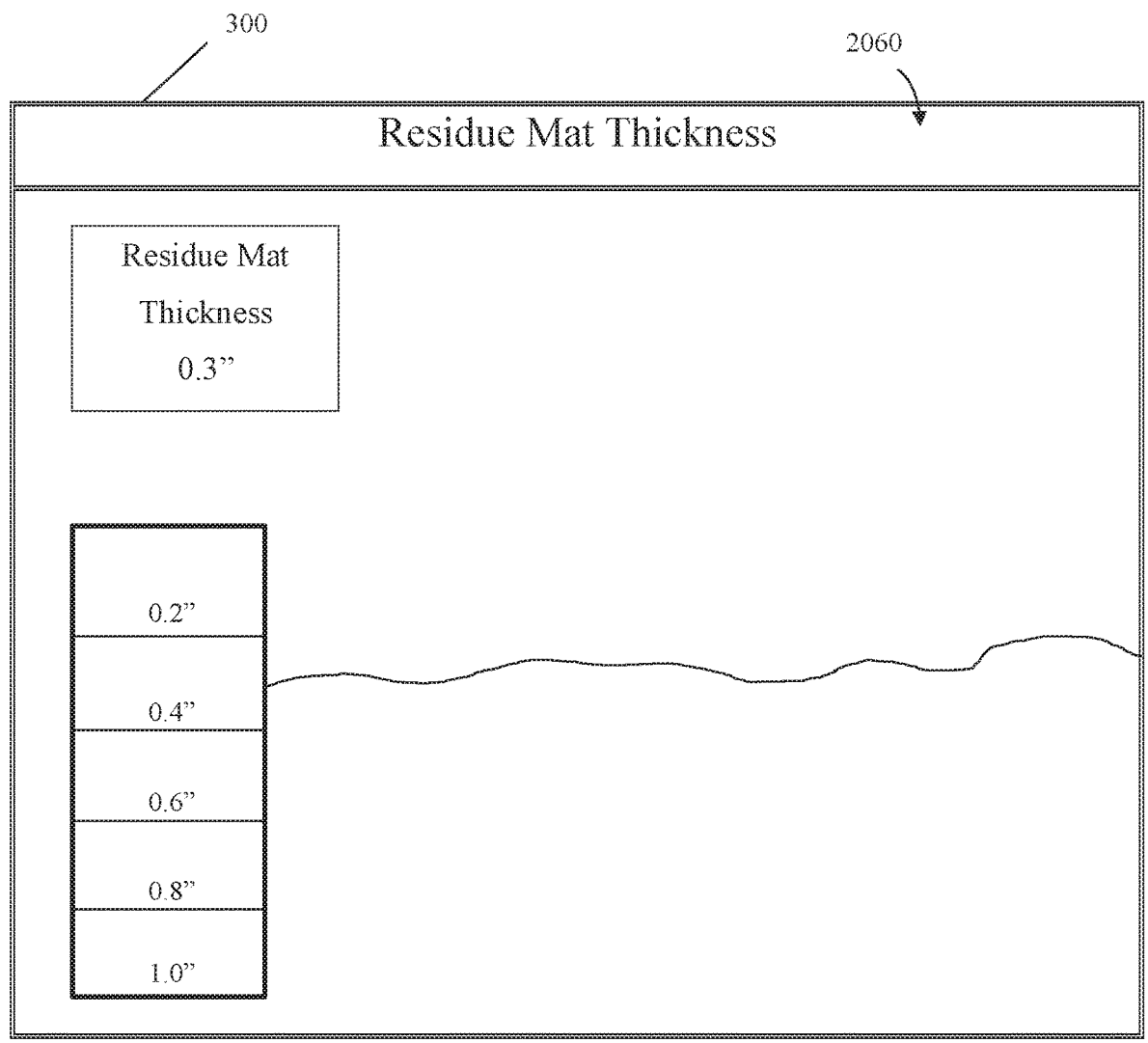
FIG. 22 illustrates a monitor displaying residue mat thickness.
Figure 23:
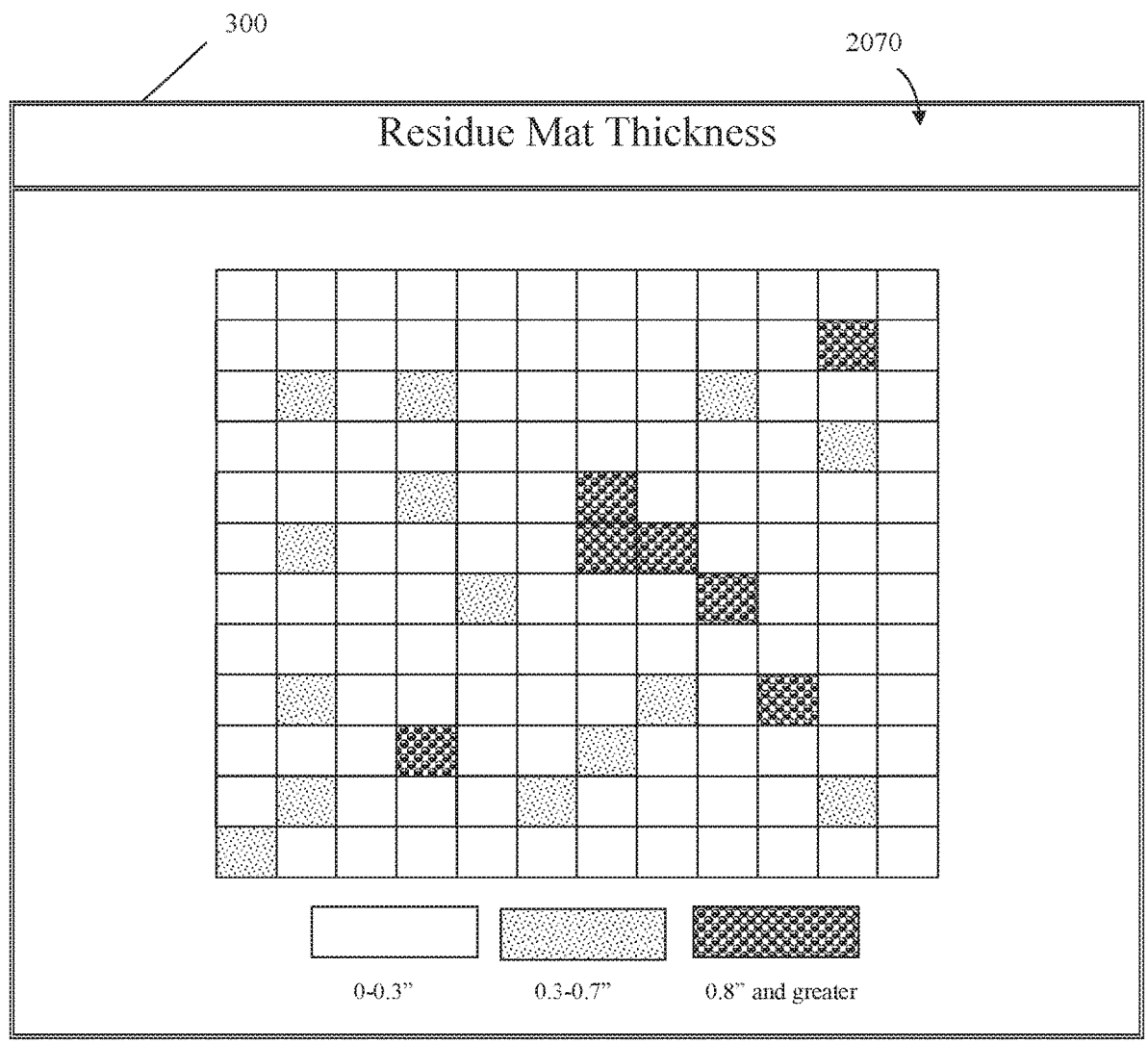
FIG. 23 illustrates a monitor spatially displaying residue mat thickness.

FIGS. 17-23 illustrate a monitor 300 displaying different measured soil data. While illustrated with some data shown together and some data shown separately for illustration purposes, any of the data can be displayed together or individually. FIG. 17 illustrates screen 2010 on monitor 300 displaying the number of different soil density layers, the density of each layer, the depth of the interface between layers, magnitude of density layer difference, and a rate of change of density. FIG. 18 illustrates screen 2020 displaying the depth of interfaces between layers as the implement is moved across the soil. FIG. 19 illustrates a screen 2030 on monitor 300 displaying a spatial map across a field for the depth of the first soil layer. The greater the depth, the more preferred. In this embodiment, the depths can be colored separately, such as green for 14-20", yellow for 8-13", and red for 1-7". FIG. 20 illustrates screen 2040 on monitor 300 displaying soil density variability and the soil density variability as the implement is moved across the field. FIG. 21 illustrates screen 2050 on monitor 300 displaying soil surface roughness and soil surface roughness as the implement is moved across the field. FIG. 22 illustrates screen 2060 on monitor 300 displaying residue mat thickness and residue mat thickness as the implement is moved across the field. FIG. 23 illustrates screen 2070 on monitor 300 spatially displaying residue mat thickness across a field. While illustrated for residue mat thickness, any of the above soil measurements can be similarly displayed spatially. Also, color can be assigned to each thickness range.

Figure 24:
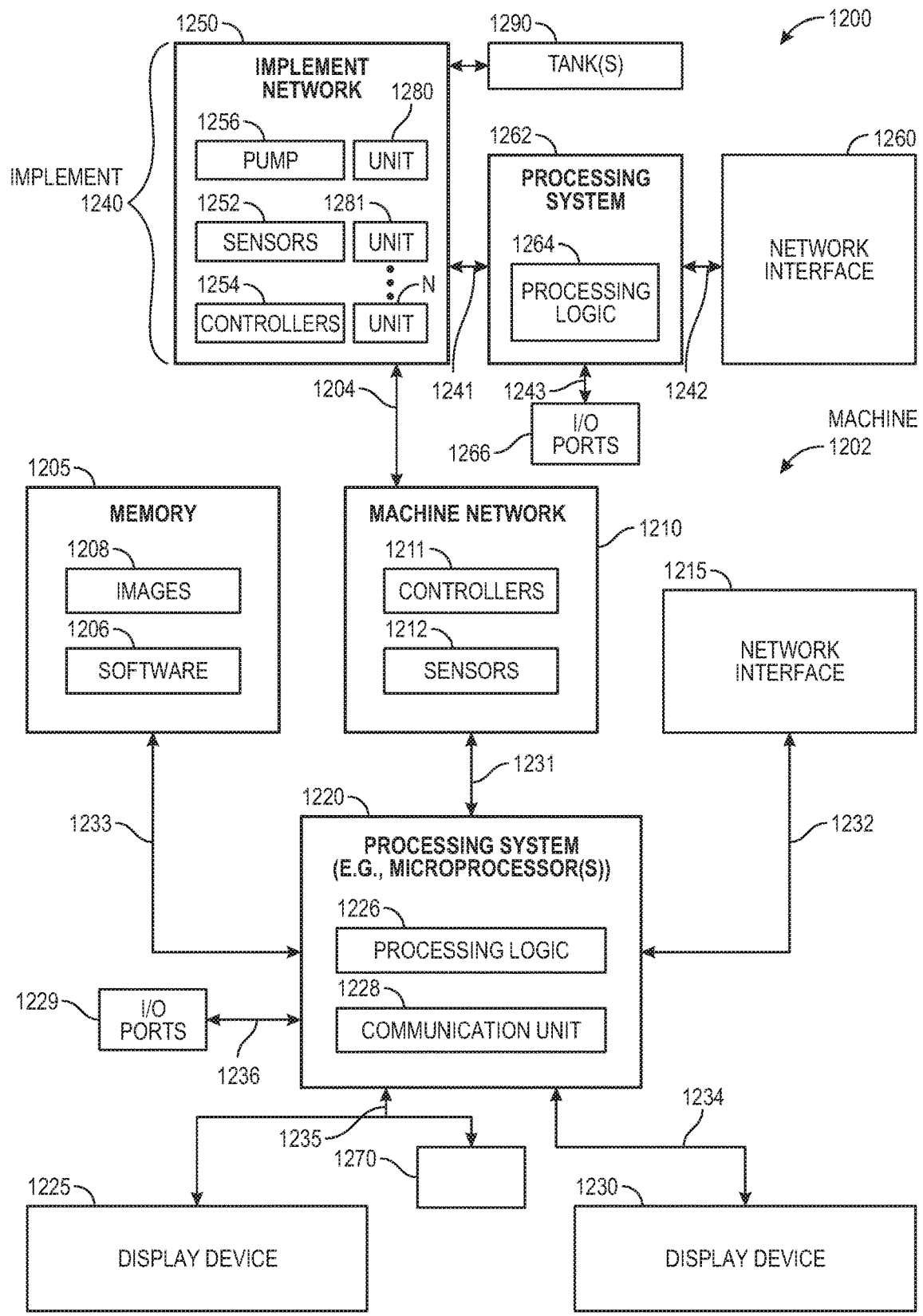
FIG. 24 shows an example of a system 1200 that includes a machine 1202 (e.g., tractor, combine harvester, etc.) and an implement 1240 (e.g., planter, sidedress bar, cultivator, plough, sprayer, spreader, irrigation implement, etc.) in accordance with one embodiment.

FIG. 24 shows an example of a system 1200 that includes a machine 1202 (e.g., tractor, combine harvester, etc.) and an implement 1240 (e.g., planter, sidedress bar, cultivator, plough, sprayer, spreader, irrigation implement, etc.) in accordance with one embodiment. The machine 1202 includes a processing system 1220, memory 1205, machine network 1210 (e.g., a controller area network (CAN) serial bus protocol network, an ISOBUS network, etc.), and a network interface 1215 for communicating with other systems or devices including the implement 1240. The machine network 1210 includes sensors 1212 (e.g., speed sensors), controllers 1211 (e.g., GPS receiver, radar unit) for controlling and monitoring operations of the machine or implement. The network interface 1215 can include at least one of a GPS transceiver, a WLAN transceiver (e.g., WiFi), an infrared transceiver, a Bluetooth transceiver, Ethernet, or other interfaces from communications with other devices and systems including the implement 1240. The network interface 1215 may be integrated with the machine network 1210 or separate from the machine network 1210 as illustrated in FIG. 12. The I/O ports 1229 (e.g., diagnostic/on board diagnostic (OBD) port) enable communication with another data processing system or device (e.g., display devices, sensors, etc.).

In one example, the machine performs operations of a tractor that is coupled to an implement for planting applications and soil sensing of a field. The planting data and soil data for each row unit of the implement can be associated with locational data at time of application to have a better understanding of the planting and soil characteristics for each row and region of a field. Data associated with the planting applications and soil characteristics can be displayed on at least one of the display devices 1225 and 1230. The display devices can be integrated with other components (e.g., processing system 1220, memory 1205, etc.) to form the monitor 300.

The processing system 1220 may include one or more microprocessors, processors, a system on a chip (integrated circuit), or one or more microcontrollers. The processing system includes processing logic 1226 for executing software instructions of one or more programs and a communication unit 1228 (e.g., transmitter, transceiver) for transmitting and receiving communications from the machine via machine network 1210 or network interface 1215 or implement via implement network 1250 or network interface 1260. The communication unit 1228 may be integrated with the processing system or separate from the processing system. In one embodiment, the communication unit 1228 is in data communication with the machine network 1210 and implement network 1250 via a diagnostic/OBD port of the I/O ports 1229.

Processing logic 1226 including one or more processors or processing units may process the communications received from the communication unit 1228 including agricultural data (e.g., GPS data, planting application data, soil characteristics, any data sensed from sensors of the implement 1240 and machine 1202, etc.). The system 1200 includes memory 1205 for storing data and programs for execution (software 1206) by the processing system. The memory 1205 can store, for example, software components such as planting application software or soil software for analysis of soil and planting applications for performing operations of the present disclosure, or any other software application or module, images (e.g., captured images of crops, soil, furrow, soil clods, row units, etc.), alerts, maps, etc. The memory 1205 can be any known form of a machine readable non-transitory storage medium, such as semiconductor memory (e.g., flash; SRAM; DRAM; etc.) or non-volatile memory, such as hard disks or solid-state drive. The system can also include an audio input/output subsystem (not shown) which may include a microphone and a speaker for, for example, receiving and sending voice commands or for user authentication or authorization (e.g., biometrics).

The processing system 1220 communicates bi-directionally with memory 1205, machine network 1210, network interface 1215, display device 1230, display device 1225, and I/O ports 1229 via communication links 1231-1236, respectively. The processing system 1220 can be integrated with the memory 1205 or separate from the memory 1205.

Display devices 1225 and 1230 can provide visual user interfaces for a user or operator. The display devices may include display controllers. In one embodiment, the display device 1225 is a portable tablet device or computing device with a touchscreen that displays data (e.g., planting application data, captured images, localized view map layer, high definition field maps of different measured soil data, as-planted or as-harvested data or other agricultural variables or parameters, yield maps, alerts, etc.) and data generated by an agricultural data analysis software application and receives input from the user or operator for an exploded view of a region of a field, monitoring and controlling field operations. The operations may include configuration of the machine or implement, reporting of data, control of the machine or implement including sensors and controllers, and storage of the data generated. The display device 1230 may be a display (e.g., display provided by an original equipment manufacturer (OEM)) that displays images and data for a localized view map layer, measured soil data, as-applied fluid application data, as-planted or as-harvested data, yield data, seed germination data, seed environment data, controlling a machine (e.g., planter, tractor, combine, sprayer, etc.), steering the machine, and monitoring the machine or an implement (e.g., planter, combine, sprayer, etc.) that is connected to the machine with sensors and controllers located on the machine or implement.

A cab control module 1270 may include an additional control module for enabling or disabling certain components or devices of the machine or implement. For example, if the user or operator is not able to control the machine or implement using one or more of the display devices, then the cab control module may include switches to shut down or turn off components or devices of the machine or implement.

The implement 1240 (e.g., planter, cultivator, plough, sprayer, spreader, irrigation implement, etc.) includes an implement network 1250, a processing system 1262, a network interface 1260, and optional input/output ports 1266 for communicating with other systems or devices including the machine 1202. The implement network 1250 (e.g., a controller area network (CAN) serial bus protocol network, an ISOBUS network, etc.) includes a pump 1256 for pumping fluid from a storage tank(s) 1290 to application units 1280, 1281, ... N of the implement, sensors 1252 (e.g., radar, electroconductivity, electromagnetic, a force probe, speed sensors, seed sensors for detecting passage of seed, sensors for detecting characteristics of soil or a trench including a plurality of soil layers differing by density, a depth of a transition from a first soil layer to a second soil layer based on density of each layer, a magnitude of a density layer difference between soil layers, a rate of change of soil density across a depth of soil, soil density variability, soil surface roughness, residue mat thickness, a density at a soil layer, soil temperature, seed presence, seed spacing, percentage of seeds firmed, and soil residue presence, at least one optical sensor to sense at least one of soil organic matter, soil moisture, soil texture, and soil cation-exchange capacity (CEC), downforce sensors, actuator valves, moisture sensors or flow sensors for a combine, speed sensors for the machine, seed force sensors for a planter, fluid application sensors for a sprayer, or vacuum, lift, lower sensors for an implement, flow sensors, etc.), controllers 1254 (e.g., GPS receiver), and the processing system 1262 for controlling and monitoring operations of the implement. The pump controls and monitors the application of the fluid to crops or soil as applied by the implement. The fluid application can be applied at any stage of crop development including within a planting trench upon planting of seeds, adjacent to a planting trench in a separate trench, or in a region that is nearby to the planting region (e.g., between rows of corn or soybeans) having seeds or crop growth.

For example, the controllers may include processors in communication with a plurality of seed sensors. The processors are configured to process data (e.g., fluid application data, seed sensor data, soil data, furrow or trench data) and transmit processed data to the processing system 1262 or 1220. The controllers and sensors may be used for monitoring motors and drives on a planter including a variable rate drive system for changing plant populations. The controllers and sensors may also provide swath control to shut off individual rows or sections of the planter. The sensors and controllers may sense changes in an electric motor that controls each row of a planter individually. These sensors and controllers may sense seed delivery speeds in a seed tube for each row of a planter.

The network interface 1260 can be a GPS transceiver, a WLAN transceiver (e.g., WiFi), an infrared transceiver, a Bluetooth transceiver, Ethernet, or other interfaces from communications with other devices and systems including the machine 1202. The network interface 1260 may be integrated with the implement network 1250 or separate from the implement network 1250 as illustrated in FIG. 24.

The processing system 1262 communicates bi-directionally with the implement network 1250, network interface 1260, and I/O ports 1266 via communication links 1241-1243, respectively.

The implement communicates with the machine via wired and possibly also wireless bi-directional communications 1204. The implement network 1250 may communicate directly with the machine network 1210 or via the network interfaces 1215 and 1260. The implement may also by physically coupled to the machine for agricultural operations (e.g., soil sensing, planting, harvesting, spraying, etc.).

The memory 1205 may be a machine-accessible non-transitory medium on which is stored one or more sets of instructions (e.g., software 1206) embodying any one or more of the methodologies or functions described herein. The software 1206 may also reside, completely or at least partially, within the memory 1205 and/or within the processing system 1220 during execution thereof by the system 1200, the memory and the processing system also constituting machine-accessible storage media. The software 1206 may further be transmitted or received over a network via the network interface 1215.

In one embodiment, a machine-accessible non-transitory medium (e.g., memory 1205) contains executable computer program instructions which when executed by a data processing system cause the system to performs operations or methods of the present disclosure. While the machine-accessible non-transitory medium (e.g., memory 1205) is shown in an exemplary embodiment to be a single medium, the term "machine-accessible non-transitory medium" should be taken to include a single medium or multiple media (e.g., a centralized or distributed database, and/or associated caches and servers) that store the one or more sets of instructions. The term "machine-accessible non-transitory medium" shall also be taken to include any medium that is capable of storing, encoding or carrying a set of instructions for execution by the machine and that cause the machine to perform any one or more of the methodologies of the present disclosure. The term "machine-accessible non-transitory medium" shall accordingly be taken to include, but not be limited to, solid-state memories, optical and magnetic media, and carrier wave signals.

Any of the following examples can be combined into a single embodiment or these examples can be separate embodiments. In one example of a first embodiment, a soil sensing system comprises an agricultural implement and at least one sensor disposed on the agricultural implement. The sensor generates an electromagnetic field through a region of soil of interest as the agricultural implement traverses a field. The sensor comprises at least one radar transmitter and at least one radar receiver or a transceiver and the sensor measures a soil dielectric constant of the region of soil of interest.

In another example of the first embodiment, the soil sensing system further comprises a monitor in communication with the sensor and adapted to generate a numeric display or a spatial mapping of the soil dielectric constant for a region of a field based on the generated electromagnetic field through the region of interest.

In another example of the first embodiment, the implement comprises a planter.

In another example of the first embodiment, the implement comprises one of a tractor, a planter, a seeder, a tillage tool, a combine, a sprayer, and an agricultural toolbar.

In another example of the first embodiment, the sensor to measure or calculate at least one of the presence of one or more soil densities existing between 0 and 30 inches of soil depth, a magnitude of the density layer differences or a magnitude of the soil densities, a rate of change of the soil density layer changes, and a soil depth at which each density layer starts or transitions to a different density layer.

In another example of the first embodiment, the sensor to measure or calculate a soil density change at a certain depth and a sensed moisture level at this depth or combined with soil type or texture to process raw data to generate processed data.

In another example of the first embodiment, the sensor to measure or calculate at least one of soil density variability, soil surface roughness that is measured as Coefficient of Variation, and a residual material thickness.

In another example of the first embodiment, the sensor generates the electromagnetic field having a frequency range of 10 MHz to 2.6 GHz.

In one example of a second embodiment, an implement comprises a first radar transceiver or a combination of a first radar transmitter and first radar receiver for sensing soil properties at a first depth of soil and a second radar transceiver or a combination of a second radar transmitter and second radar receiver for sensing soil properties at a second depth of soil.

In another example of the second embodiment, the implement comprises one of a tractor, a planter, a seeder, a tillage tool, a combine, a sprayer, and an agricultural toolbar.

In another example of the second embodiment, the implement comprises a planter.

In another example of the second embodiment, the implement further comprises a monitor in communication with the first radar transceiver or a combination of the first radar transmitter and first radar receiver and the second radar transceiver or a combination of the second radar transmitter and second radar receiver and adapted to generate a numeric display or a spatial mapping of the soil at the first depth and the second depth.

In another example of the second embodiment, the implement further comprises an electrical conductivity sensor to sense electrical conductivity of soil with the electrical conductivity corresponding to a soil dielectric constant.

In one example of a third embodiment, a soil sensing system for sensing soil properties comprises an implement, a radar transceiver or a combination of radar transmitter and a radar receiver disposed on the implement for sensing soil properties at a depth of soil and at least one optical sensor to sense at least one of soil organic matter, soil moisture, soil texture, and soil cation-exchange capacity (CEC).

In another example of the third embodiment, the implement is one of a tractor, a planter, a seeder, a tillage tool, a combine, a sprayer, and an agricultural toolbar.

In another example of the third embodiment, the implement is a planter.

In another example of the third embodiment, the soil sensing system further comprises a monitor in communication with the radar transceiver or a combination of the radar transmitter and the radar receiver and the optical sensor and adapted to generate a numeric display or a spatial mapping of the soil.

In one example of a fourth embodiment, a soil sensing system comprises an agricultural implement and at least one sensor disposed on the agricultural implement and directed to soil to measure at least one of:
 a plurality of soil layers differing by density; a depth of a transition from a first soil layer to a second soil layer based on density of each layer; a magnitude of a density layer difference between soil layers; a rate of change of soil density across a depth of soil; soil density variability; soil surface roughness; residue mat thickness; and a density at a soil layer.

In another example of the fourth embodiment, the sensor is one of radar, electroconductivity, electromagnetic, and a force probe.

In another example of the fourth embodiment, the agricultural implement is one of a tractor, a planter, a seeder, a tillage tool, a combine, a sprayer, and an agricultural toolbar.

In another example of the fourth embodiment, the soil sensing system further comprises a monitor in communication with the sensor and adapted to generate a numeric display or a spatial mapping of the soil.

In another example of the fourth embodiment, the soil sensing system further comprises a common midpoint (CMP) antenna array that is utilized by positioning a target at a known depth, transmitting electromagnetic pulses into soil, receiving electromagnetic pulses, and then calculating for that depth.

Figure 25:
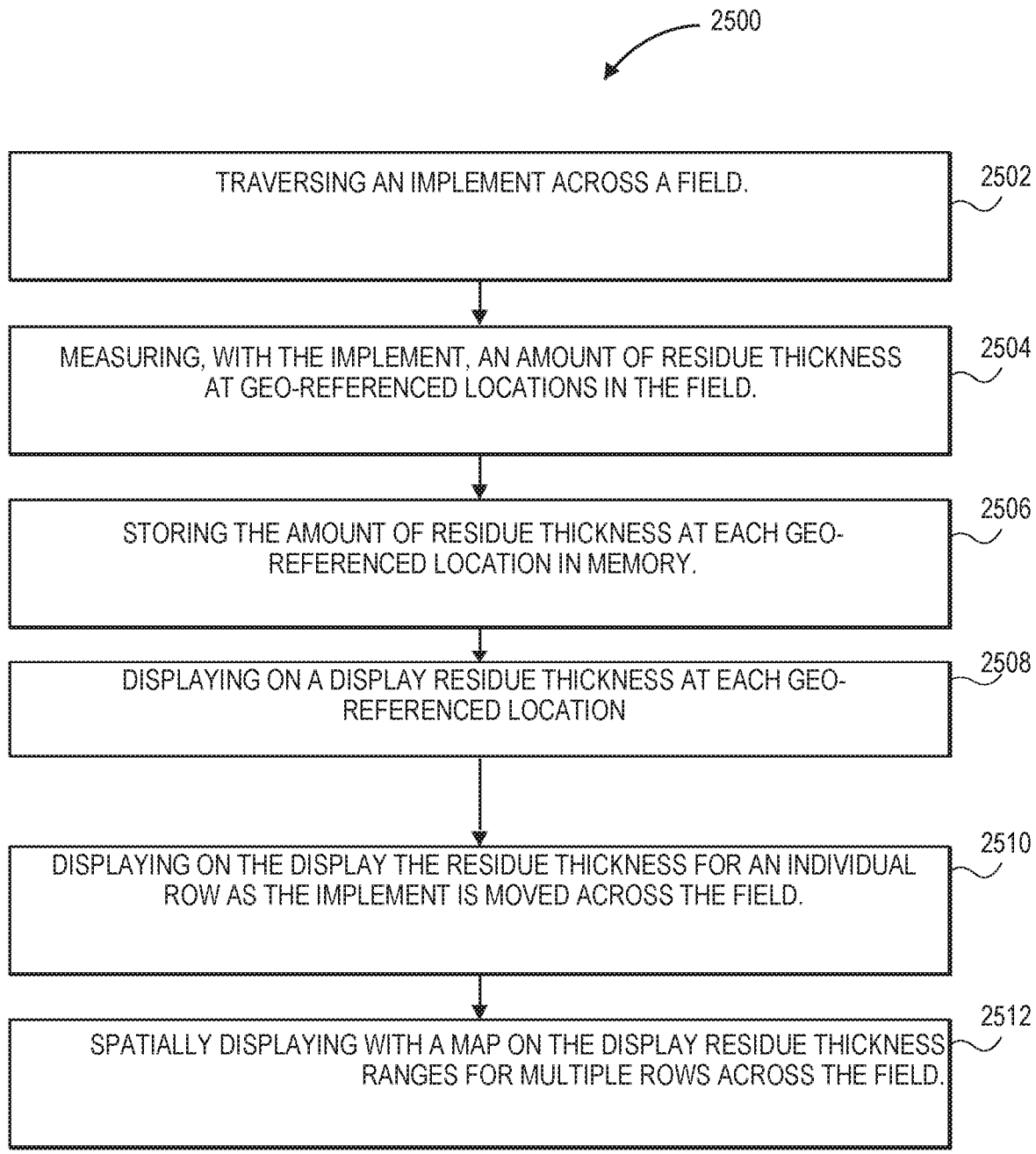
FIG. 25 illustrates a method 2500 of measuring residue mat thickness of residue in a field.

In one example of a fifth embodiment as illustrated in FIG. 25, a method 2500 of measuring residue mat thickness of residue in a field comprises traversing an implement across a field at operation 2502. A radar transceiver or a combination of radar transmitter and a radar receiver is disposed on the implement for sensing residue on the field. At operation 2504, the method includes measuring, with the implement, an amount of residue thickness at geo-referenced locations in the field, and storing the amount of residue thickness at each geo-referenced location in memory at operation 2506.

In another example of the fifth embodiment, the method further comprises displaying on a display residue thickness at each geo-referenced location at operation 2508.

In another example of the fifth embodiment, the method further comprises displaying on the display as illustrated in FIG. 22 the residue thickness for an individual row as the implement is moved across the field at operation 2510.

In another example of the fifth embodiment, the method further comprises spatially displaying with a map on the display as illustrated in FIG. 23 residue thickness ranges for multiple rows across the field at operation 2512.

In another example of the fifth embodiment, the implement is one of a tractor, a planter, a seeder, a tillage tool, a combine, a sprayer, and an agricultural toolbar.

Figure 26:
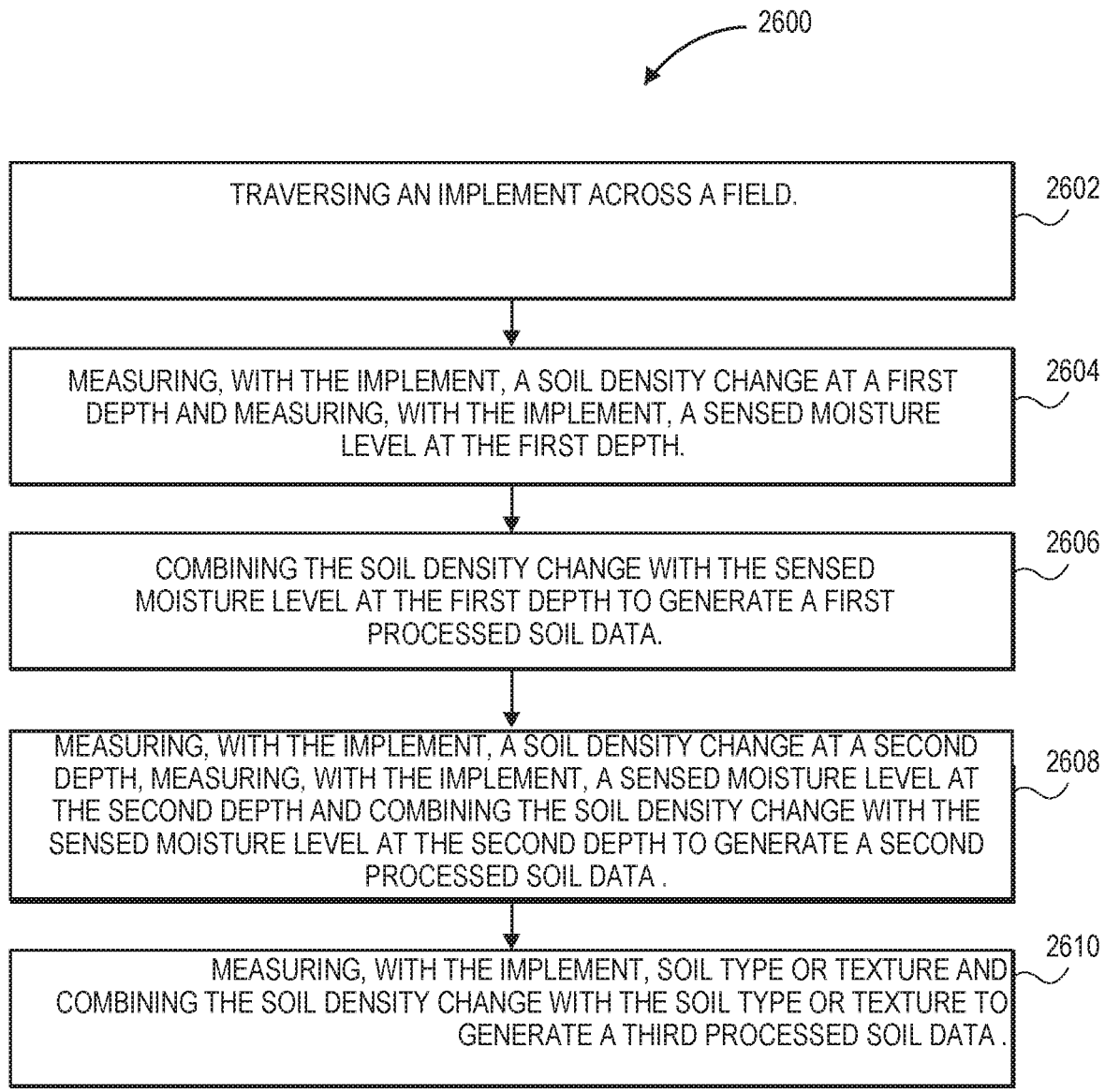
FIG. 26 illustrates a method 2600 to generate processed soil data.

In one example of a sixth embodiment as illustrated in FIG. 26, a method 2600 to generate processed soil data (e.g., processed soil data of FIG. 16B) comprises traversing an implement across a field at operation 2602. A radar transceiver or a combination of radar transmitter and a radar receiver is disposed on the implement for sensing soil characteristics of the field. At operation 2604, the method includes measuring, with the implement, a soil density change at a first depth. At operation 2606, the method further includes combining the soil density change with the sensed moisture level at the first depth to generate a first processed soil data.

In another example of the sixth embodiment, the method further comprises measuring, with the implement, a soil density change at a second depth, measuring, with the implement, a sensed moisture level at the second depth and combining the soil density change with the sensed moisture level at the second depth to generate a second processed soil data at operation 2608.

In another example of the sixth embodiment, a depth of roots during harvest for in row versus out of row are determined based on soil density.

In another example of the sixth embodiment, the method further comprises measuring, with the implement, soil type or texture and combining the soil density change with the soil type or texture to generate a third processed soil data at operation 2610.

Figure 27:
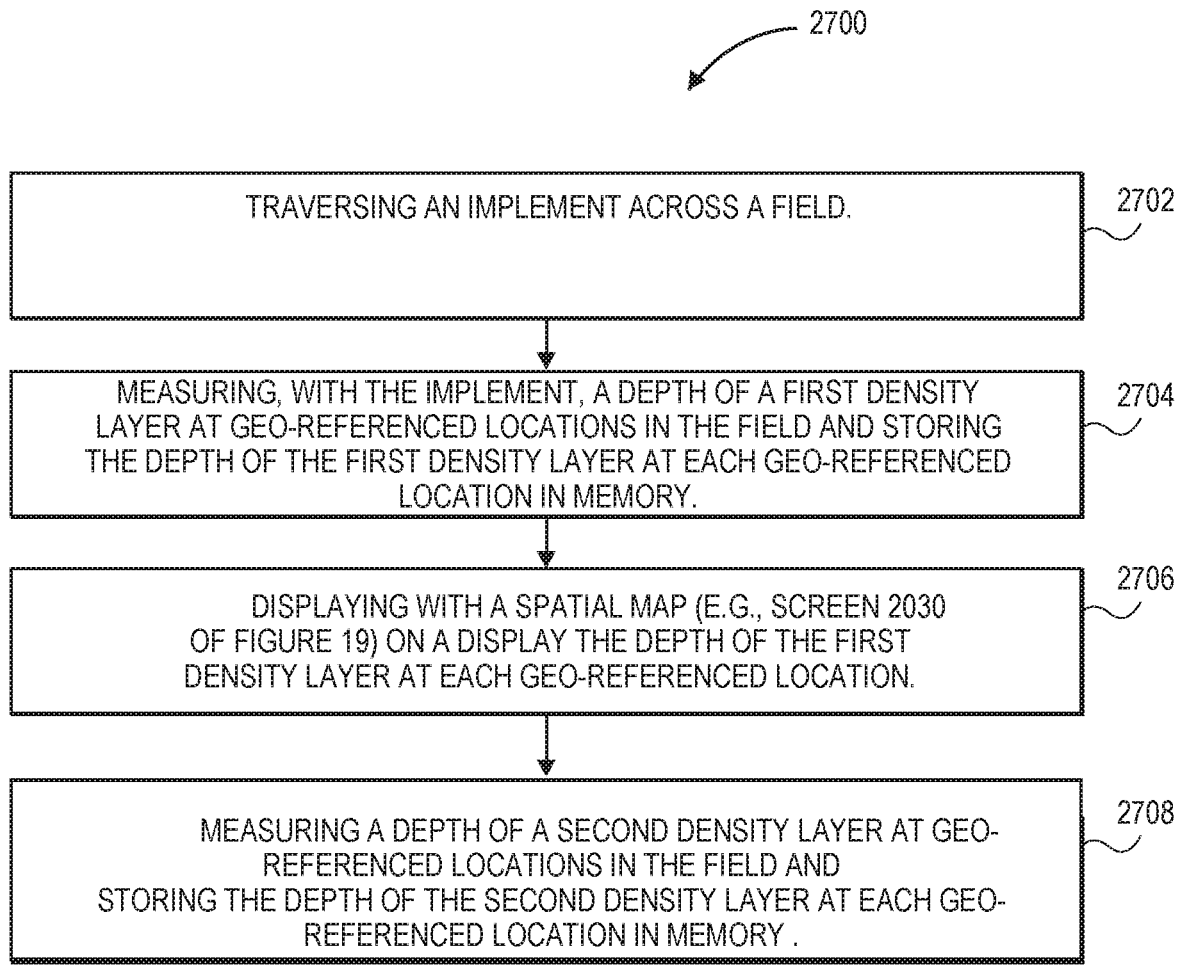
FIG. 27 illustrates a method 2700 of measuring soil characteristics in a field.

In one example of a seventh embodiment as illustrated in FIG. 27, a method 2700 of measuring soil characteristics in a field comprises traversing an implement across a field at operation 2702. A radar transceiver or a combination of radar transmitter and a radar receiver is disposed on the implement for sensing soil characteristics of the field. At operation 2704, the method includes measuring, with the implement, a depth of a first density layer at geo-referenced locations in the field and storing the depth of the first density layer at each geo-referenced location in memory.

In another example of the seventh embodiment, the method further comprises displaying with a spatial map (e.g., screen 2030 of FIG. 19) on a display the depth of the first density layer at each geo-referenced location at operation 2706.

In another example of the seventh embodiment, the method further comprises measuring a depth of a second density layer at geo-referenced locations in the field and storing the depth of the second density layer at each geo-referenced location in memory at operation 2708.

What is claimed is:

1. A soil sensing system comprising:
   an agricultural implement; and
   at least one sensor disposed on the agricultural implement and remotely located from a region of soil of interest, the sensor generating an electromagnetic field through the region of soil of interest as the agricultural implement traverses a field, wherein the sensor comprises at least one radar transmitter and at least one radar receiver or a transceiver and the sensor is configured to determine or measure a soil dielectric constant of the region of soil of interest, wherein the agricultural implement comprises one of a tractor, a planter, a seeder, a tillage tool, a combine, and a sprayer, wherein the sensor is configured to measure soil data to determine at least one of a magnitude of a density layer difference between soil layers and a rate of change of a soil density across a depth of soil based on the soil dielectric constant.

2. The soil sensing system of claim 1, further comprising:
   a monitor in communication with the sensor and adapted to generate a numeric display including an average or current value of the soil dielectric constant or a spatial mapping of the soil dielectric constant for a region of a field based on the generated electromagnetic field through the region of interest.

3. The soil sensing system of claim 1, wherein the agricultural implement comprises a planter, wherein the sensor comprises a ground penetrating radar system having multiple radar antennas for measuring a soil dielectric constant of the region of soil of interest.

4. The soil sensing system of claim 1, wherein the sensor is configured to measure soil data including images of a soil subsurface based on detecting reflected signals from subsurface structures or a boundary between soil layers having different permittivities.

5. The soil sensing system of claim 1, wherein the sensor is configured to measure or calculate at least one of one or more soil densities existing between 0 and 30 inches of soil depth, a magnitude of the one or more soil densities, and a soil depth at which a density layer starts or transitions to a different density layer.

6. The soil sensing system of claim 5, wherein the sensor is configured to measure or calculate a soil density change at a certain depth and a sensed moisture level at this depth or combined with soil type or texture to process raw data to generate processed data.

7. The soil sensing system of claim 1, wherein the sensor is configured to measure or calculate at least one of soil density variability, soil surface roughness that is measured as Coefficient of Variation, and a residual material thickness.

8. The soil sensing system of claim 1, wherein the sensor generates the electromagnetic field having a frequency range of 10 MHz to 2.6 GHz.

* * * * *